(12) United States Patent
Stern et al.

(10) Patent No.: US 11,914,791 B2
(45) Date of Patent: Feb. 27, 2024

(54) GESTURE CONTROL USING BIOPOTENTIAL-BASED ANALOG FRONT END

(71) Applicant: Pison Technology, Inc., Boston, MA (US)

(72) Inventors: Kenneth Stern, Newton Lower Falls, MA (US); Tanya Wang, Wakefield, RI (US); Tristan McLaurin, Cambridge, MA (US); David Cipoletta, Boston, MA (US); Dexter Ang, Boston, MA (US)

(73) Assignee: Pison Technology, Inc., Boston, MA (US)

( * ) Notice: Subject to any disclaimer, the term of this patent is extended or adjusted under 35 U.S.C. 154(b) by 0 days.

(21) Appl. No.: 17/935,480

(22) Filed: Sep. 26, 2022

(65) Prior Publication Data

US 2023/0019413 A1    Jan. 19, 2023

Related U.S. Application Data

(63) Continuation-in-part of application No. 17/933,287, filed on Sep. 19, 2022, now Pat. No. 11,762,473, (Continued)

(51) Int. Cl.
*G06F 3/01* (2006.01)
*G06F 1/16* (2006.01)
(Continued)

(52) U.S. Cl.
CPC .............. *G06F 3/017* (2013.01); *G06F 1/163* (2013.01); *G06F 3/013* (2013.01); *H04W 4/021* (2013.01);
(Continued)

(58) Field of Classification Search
CPC ........ G06F 3/017; G06F 1/163; H04W 4/029; H04W 4/027
See application file for complete search history.

(56) References Cited

U.S. PATENT DOCUMENTS 11,367,519 B1 *  6/2022  Heldman ............... A61M 5/142
2015/0309582 A1 * 10/2015  Gupta .................... G06F 3/011
                                                    345/156

(Continued)

*Primary Examiner* — Matthew A Eason
*Assistant Examiner* — Chayce R Bibbee
(74) *Attorney, Agent, or Firm* — Scale LLP

(57) ABSTRACT

Disclosed are methods, systems and non-transitory computer readable memory for gesture control. For instance, a system may include a wearable device configured to be worn on a portion of an arm of a user. The wearable device may include a plurality of electrodes disposed on an interior of the wearable device and configured to obtain biopotential signals from the user's arm; and a biopotential chip. The biopotential microchip may be configured to output, directly or indirectly, biopotential data, acceleration data, and/or angular rate data, or derivatives thereof ("gesture data"), to a machine learning classifier. The machine learning classifier may be configured to generate, based on the gesture data, a gesture output indicating a gesture performed by the user. In some cases, the plurality of electrodes may include one or more wristband electrodes and/or a plurality of hub electrodes in a hub. In some cases, the hub may be curved.

20 Claims, 27 Drawing Sheets

Related U.S. Application Data which is a continuation of application No. 17/682,371, filed on Feb. 28, 2022, now Pat. No. 11,449,150, which is a continuation of application No. 17/384,527, filed on Jul. 23, 2021, now Pat. No. 11,262,851, which is a continuation of application No. 16/890,507, filed on Jun. 2, 2020, now Pat. No. 11,157,086, which is a continuation-in-part of application No. 16/774,825, filed on Jan. 28, 2020, now abandoned.

(51) Int. Cl.
*H04W 4/029* (2018.01)
*H04W 4/021* (2018.01)
*H04W 4/02* (2018.01)

(52) U.S. Cl.
CPC ........... *H04W 4/026* (2013.01); *H04W 4/027* (2013.01); *H04W 4/029* (2018.02)

(56) References Cited

U.S. PATENT DOCUMENTS

| | | | | |
|---|---|---|---|---|
| 2018/0338720 | A1* | 11/2018 | Gupta | G06F 1/163 |
| 2018/0360341 | A1* | 12/2018 | Wang | A61B 5/0008 |
| 2019/0324572 | A1* | 10/2019 | Tan | G06F 3/044 |
| 2021/0193977 | A1* | 6/2021 | Reykhert | A61B 5/6833 |

* cited by examiner

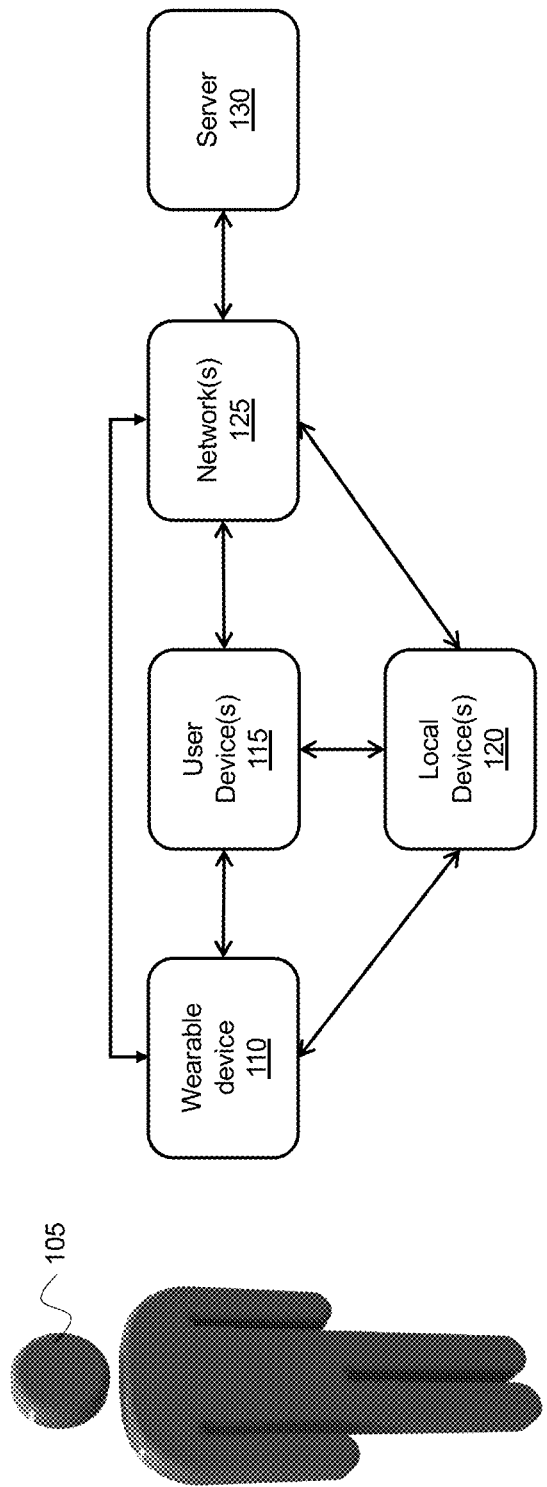

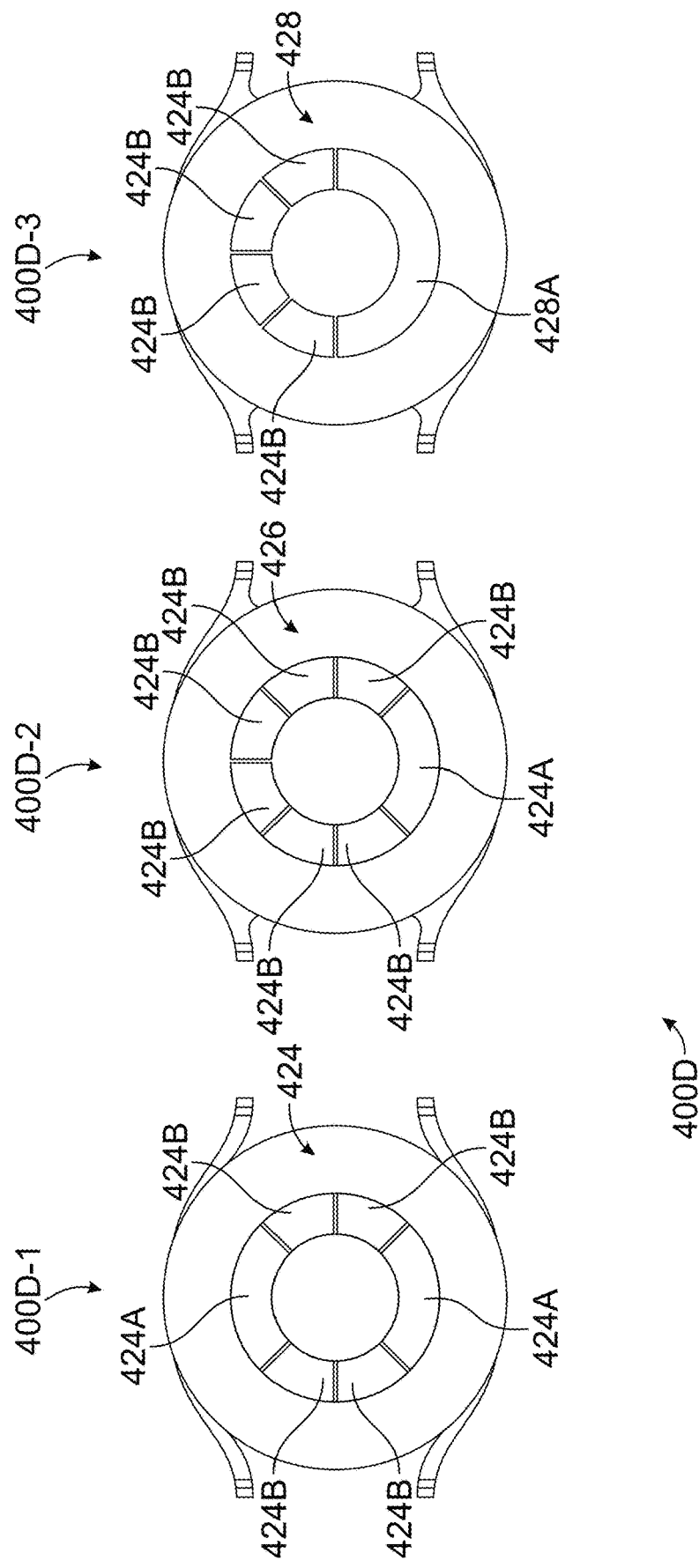

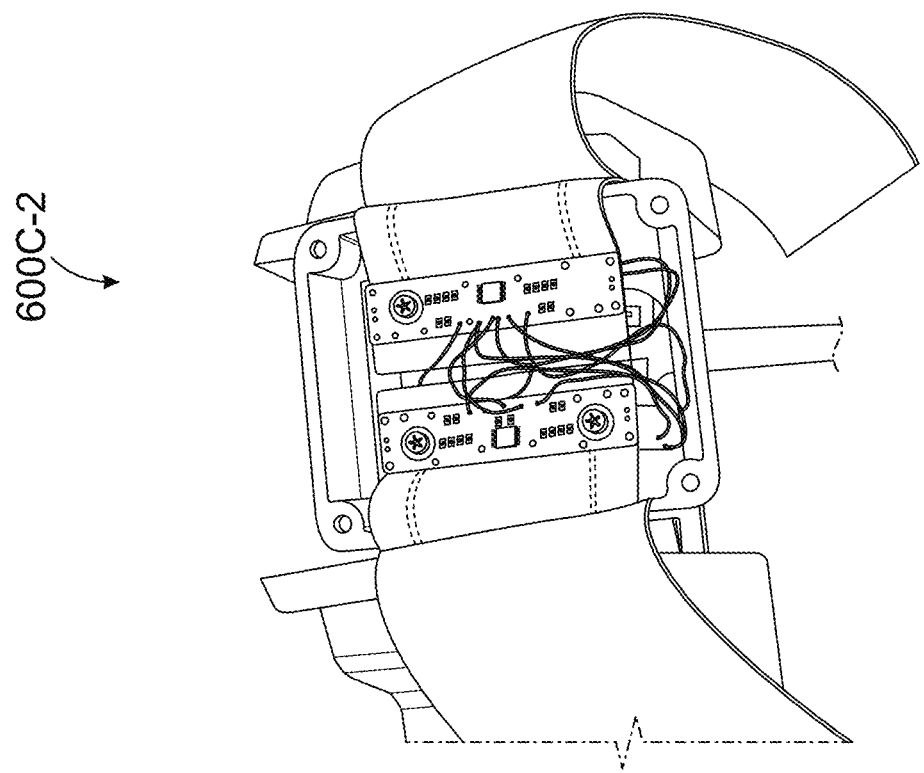
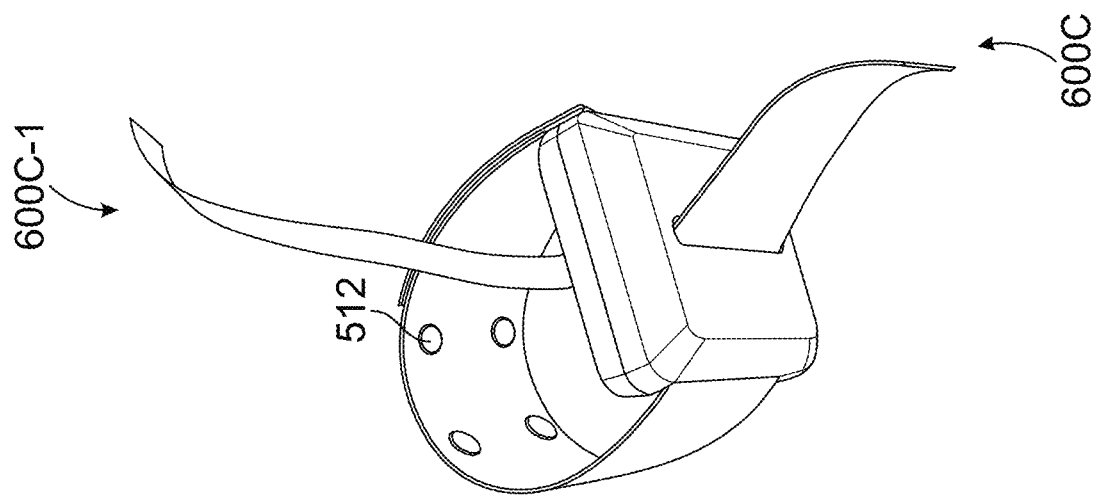
FIG. 6C

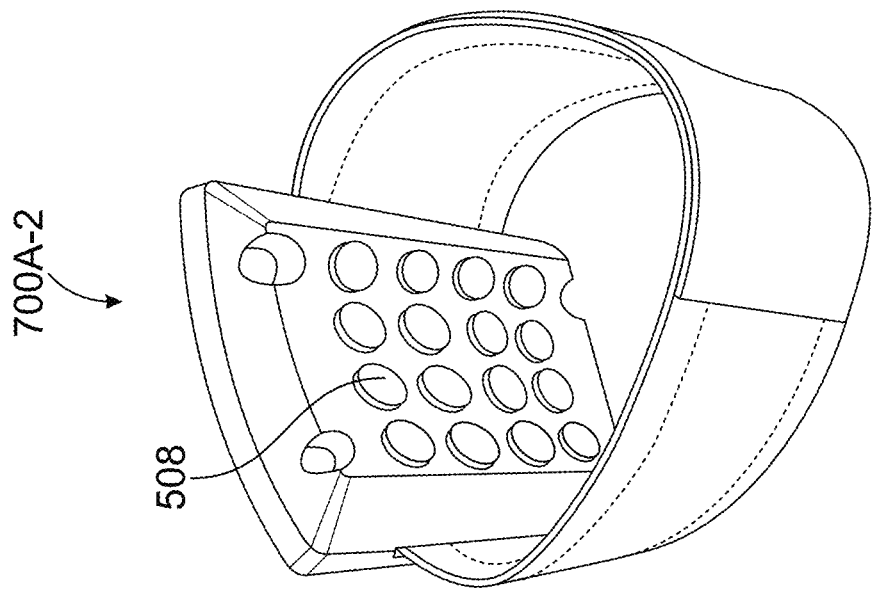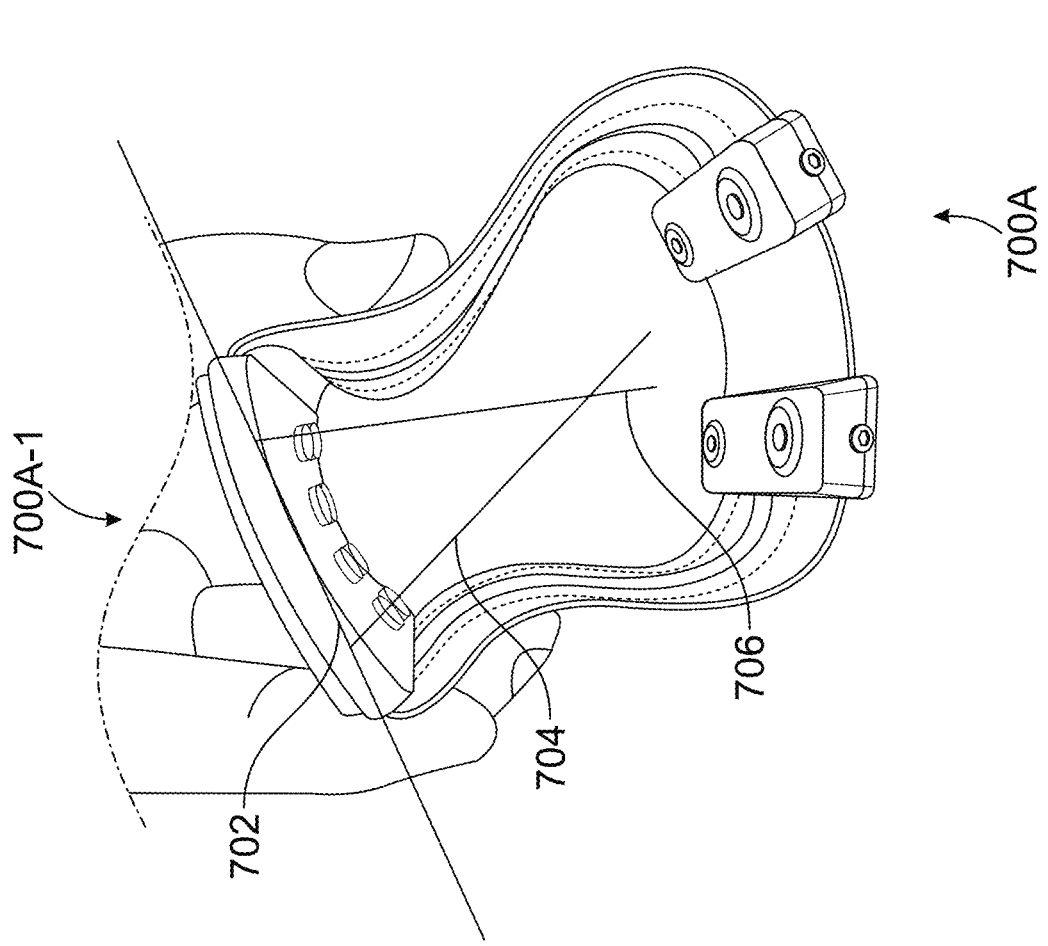
FIG. 7A

GESTURE CONTROL USING BIOPOTENTIAL-BASED ANALOG FRONT END

CROSS-REFERENCE TO RELATED APPLICATIONS

This application is a continuation-in-part of U.S. patent application Ser. No. 17/933,287, filed Sep. 19, 2022.

U.S. patent application Ser. No. 17/933,287, filed Sep. 19, 2022, is continuation of U.S. patent application Ser. No. 17/682,371, filed Feb. 28, 2022, now U.S. Pat. No. 11,449,150, issued Sep. 20, 2022.

U.S. patent application Ser. No. 17/682,371, filed Feb. 28, 2022, is a continuation of U.S. patent application Ser. No. 17/384,527, filed Jul. 23, 2021, now U.S. Pat. No. 11,262,851, issued Mar. 1, 2022.

U.S. patent application Ser. No. 17/384,527, filed Jul. 23, 2021, is a continuation of U.S. patent application Ser. No. 16/890,507, filed Jun. 2, 2020, now U.S. Pat. No. 11,157,086, issued Oct. 26, 2021.

U.S. patent application Ser. No. 16/890,507, filed Jun. 2, 2020, is a continuation-in-part of U.S. patent application Ser. No. 16/774,825, filed Jan. 28, 2020.

This application is related to U.S. patent application Ser. No. 16/104,273, filed Aug. 17, 2018. U.S. patent application Ser. No. 16/104,273, filed Aug. 17, 2018, is a continuation of U.S. patent application Ser. No. 15/826,131, filed, Nov. 29, 2017, now U.S. Pat. No. 10,070,799, issued Sep. 11, 2018. U.S. patent application Ser. No. 15/826,131, filed, Nov. 29, 2017, is a nonprovisional application of U.S. provisional patent application 62/566,674, filed Oct. 7, 2017, and U.S. provisional patent application 62/429,334, filed Dec. 2, 2016.

This application also is related to U.S. patent application Ser. No. 16/055,123, filed Aug. 5, 2018.

This application also is related to U.S. patent application Ser. No. 16/246,964, filed Jan. 14, 2019.

This application also is related to PCT Patent application serial number PCT/US19/061421, filed Nov. 4, 2019, which is an international application designating the United States claiming priority to U.S. patent application Ser. No. 16/196,462, filed Nov. 20, 2018.

This application also is related to U.S. patent application Ser. No. 16/737,252, filed Jan. 8, 2020.

All of the foregoing are hereby incorporated by reference.

TECHNICAL FIELD

Various aspects of the present disclosure relate generally to systems and methods for gesture control using biopotential sensing wearable devices and, more particularly, to systems and methods for gesture control using biopotential sensing wearable devices which include a biopotential chip and a plurality of electrodes in a hub and/or embedded in a wristband.

BACKGROUND

Generally, gesture control may rely on gesture data. Arrangement and placement of electrodes of biopotential sensing wearable devices to gather biopotential signals may be a challenge. Moreover, in some cases depending on form factor, biopotential chips of biopotential sensing wearable devices have limited surface area and/or volume to gather not only the biopotential signals but also other relevant data (e.g., acceleration data and/or angular rate data), thus an arrangement of signal processing components may also be a challenge.

The present disclosure is directed to overcoming one or more of these above-referenced challenges.

SUMMARY OF THE DISCLOSURE

According to certain aspects of the disclosure, systems, methods, and computer readable memory are disclosed for gesture control using biopotential sensing wearable devices.

For instance, a system for gesture control may include: a wearable device configured to be worn on a portion of an arm of a user. The wearable device may include: a plurality of electrodes disposed on an interior of the wearable device and configured to obtain biopotential signals from the user's arm; and a biopotential microchip. The biopotential microchip may include: one or more analog inputs configured to be coupled to and receive the biopotential signals from the plurality of electrodes, at least one of the one or more analog inputs being coupled to a respective differential amplifier configured to amplify differences in signals between pairs of electrodes; one or more analog-to-digital converters (ADCs), the one or more ADCs being configured to convert the biopotential signals to biopotential data; an accelerometer, the accelerometer being disposed onboard the biopotential microchip and configured to output acceleration data indicating an acceleration of the portion of the user's arm; a gyroscope, the gyroscope being disposed onboard the biopotential microchip and configured to output angular rate data indicating an angular rate of the portion of the user's arm; and a processor. The processor may be configured to process the biopotential data outputted by the one or more ADCs, the acceleration data outputted by the accelerometer, and the angular rate data outputted by the gyroscope. The biopotential microchip may be configured to output, directly or indirectly, the biopotential data outputted by the one or more ADCs, the acceleration data outputted by the accelerometer, and the angular rate data outputted by the gyroscope, or derivatives thereof (collectively, the gesture data), to a machine learning classifier. The machine learning classifier may be configured to generate, based on the gesture data, a gesture output indicating a gesture performed by the user.

For instance, a system for gesture control may include: a wearable device configured to be worn on a wrist of a user. The wearable device may include: a hub and a wristband. The hub may include: a sealed housing; a plurality of hub electrodes; and a biopotential microchip. The biopotential microchip may include a plurality of analog inputs, a plurality of analog-to-digital converters (ADCs) configured to receive signals from the plurality of analog inputs, an accelerometer, and a gyroscope. The wristband and the hub together may be configured to encircle the wrist of the user. The wristband may include one or more wristband electrodes. The sealed housing of the hub may include an electrical port, the electrical port being electrically connected to at least a first analog input of the plurality of analog inputs of the biopotential microchip. The wristband may include one or more wristband conductors, the one or more wristband conductors electrically connecting the one or more wristband electrodes to the electrical port of sealed housing of the hub. The plurality of hub electrodes are electrically connected via conductors disposed within the hub to one or more additional analog inputs of the plurality of analog inputs of the biopotential microchip. The one or more wristband electrodes are electrically connected to at least the first analog input of the plurality of analog inputs of the biopotential microchip via the wristband conductor and the electrical port of the sealed housing of the hub. The system may be configured to obtain biopotential data based on signals received by both the plurality of hub electrodes and the one or more wristband electrodes and processed by the ADCs of the biopotential microchip. The system may be configured to obtain wrist location data based on outputs from the accelerometer and the gyroscope. The system may be configured to transmit the biopotential data and the wrist location data to a machine learning classifier, the machine learning classifier being configured to analyze the biopotential data and the wrist location data to generate a gesture output indicating a gesture performed by the user.

Additional objects and advantages of the disclosed technology will be set forth in part in the description that follows, and in part will be apparent from the description, or may be learned by practice of the disclosed technology.

It is to be understood that both the foregoing general description and the following detailed description are exemplary and explanatory only and are not restrictive of the disclosed technology, as claimed.

BRIEF DESCRIPTION OF THE DRAWINGS

The accompanying drawings, which are incorporated in and constitute a part of this specification, illustrate various exemplary aspects and together with the description, serve to explain the principles of the disclosed technology.

FIG. 1 depicts an example environment for gesture control using a wearable device.

FIGS. 4A-4D depict graphics of different arrangements of hub electrodes of a wearable device.

FIGS. 6A-6D depict graphics of different aspects of wristband electrodes of a biopotential sensor.

FIGS. 7A-7B depict graphics of different aspects of hub electrodes disposed in a curved arrangement.

DETAILED DESCRIPTION

Figure 2A:
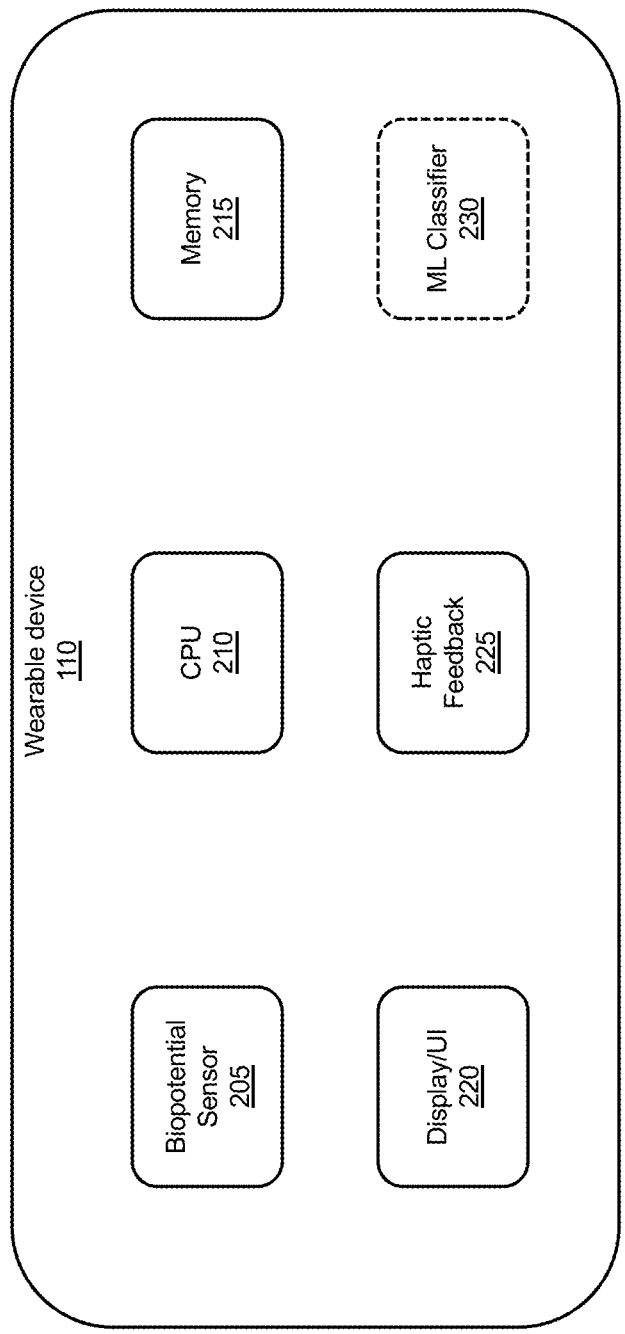
FIGS. 2A-2C depict block diagrams of aspects of a wearable device.

In general, the present disclosure is directed to methods and systems for gesture control using biopotential sensing wearable devices. As discussed in detail herein, a wearable device of the present disclosure may be configured to be worn on a portion of an arm of a user. The wearable device may include a plurality of electrodes disposed on an interior of the wearable device and configured to obtain biopotential signals from the user's arm. The wearable device may also include a biopotential chip. The biopotential chip may be configured to output, directly or indirectly, biopotential data, acceleration data, and/or angular rate data, or derivatives thereof ("gesture data"), to a machine learning classifier. The biopotential chip may include an accelerometer, a gyroscope and biopotential signal processing components on the same substrate. The machine learning classifier may be configured to generate, based on the gesture data, a gesture output indicating a gesture performed by the user.

In some cases, the biopotential device may include switches or a multiplexer to dynamically rearrange signal pathways between the plurality of electrodes and analog inputs on the biopotential chip (and/or other biopotential chips). In this manner, the wearable device may be reconfigured based on remote instructions (e.g., from a server) or over time (as a user provides feedback during training). Thus, the wearable device may improve over time without requiring hardware replacement of components.

In some cases, the plurality of electrodes may include one or more wristband electrodes and/or a plurality of hub electrodes in a hub. In this manner, the wristband electrodes may enable the wearable device to sense biopotentials away from the hub and increase a range of gesture detection.

In some cases, the hub electrodes may be arranged in a curved manner. In this manner, the hub electrodes provide increased signal quality across the hub electrodes, especially in contrast to flatly arranged hub electrodes near the edges of a hub.

Thus, methods and systems of the present disclosure may be improvements to computer technology and/or gesture detection technology using biopotential data.

Environment

FIG. 1 depicts an example environment 100 for gesture control using a wearable device 110. The environment 100 may include a user 105, the wearable device 110, a user device 115, local device(s) 120, network(s) 125, and a server 130. The wearable device 110 may obtain gesture data, so that a gesture output can be generated (e.g., by the wearable device 110, the user device 115, the server 130). The gesture output may indicate a gesture performed by the user 105. The wearable device 110, the user device 115, and/or the server 130 may then perform one or more command actions based on the gesture output, such as control remote devices (e.g., robots, UAMs, or systems), control local devices, such as the user device 115 or the local devices 120, and the like.

The user 105 may wear the wearable device 110 on a portion of an arm of the user 105, such as the wrist and/or the forearm of the user 105. The wearable device 110 may be gesture control device, a smartwatch, or other wrist or forearm wearable (e.g., a smart sleeve).

In some cases, the user device 115 may be a personal computing device, such as a cell phone, a tablet, a laptop, or a desktop computer. In some cases, the user device 115 may be an extended reality (XR) device, such as a virtual reality device, an argument reality device, a mixed reality device, and the like.

The local device(s) 120 may be other information technology devices in environments, such as the home, the office, in public, and the like. The local device(s) 120 may include speakers (e.g., smart speakers), TVs, garage doors, doors, cars, internet of things (IoT) devices that control various electrical and mechanical devices. Thus, local device(s) 120 may generally be any software controllable device or system that can receive action commands from the wearable device 110 or the user device 115 based on gesture outputs.

The network(s) 125 may include one or more local networks, private networks, enterprise networks, public networks (such as the internet), cellular networks, satellite networks, to connect the various devices in the environment 100. In some cases, the wearable device 110 may connect to server 130 (or local device 120) via the user device 115 and/or network(s) 125, while in some cases the wearable device 110 may connect to the server 130 (or a local device 120) directly or via the network(s) 125. For instance, in some cases, the wearable device 110 may connect to the local device 120 over a short range communication standard (such as Bluetooth or WIFI) and connect to the server 130 via a longer range communication standard (such as 4G, 5G, or 6G cellular communications, or satellite communications).

The server 130 may perform certain actions, such as host ML classifiers, provide software updates to components of the environment 100, and provide personalization data for the wearable device 110. In the case of hosting ML classifiers, the server 130 may receive requests from the wearable device 110 (e.g., via user device 115 or not) to generate a gesture output (e.g., using a certain ML classifier) based on gesture data; process the request to generate the gesture output; and transmit the gesture output and/or an action command based on the gesture output to the wearable device 110. In some cases, the user device 115 may host ML classifiers and perform the same process for the wearable device 110. In some cases, the wearable device 110 may host the ML classifiers and perform the process onboard the wearable device 110.

In the case of providing software updates to components of the environment 100, the server 130 may transmit software updates and/or ML classifiers updates to the wearable device 110 (e.g., to change certain features thereon), transmit software features and/or ML classifiers updates to the user device 115 (e.g., to change certain features thereon), and/or transmit software updates to the local device(s) 120 (to change certain features thereon). In some cases, the software updates may change what gesture output corresponds to what action command. In some cases, for the wearable device 110, the software updates may change how biopotential signals are processed onboard the wearable device 110, such configurations of connection states (as discussed herein), how encryption is handled, how communications are handled, and the like.

Figure 2B:
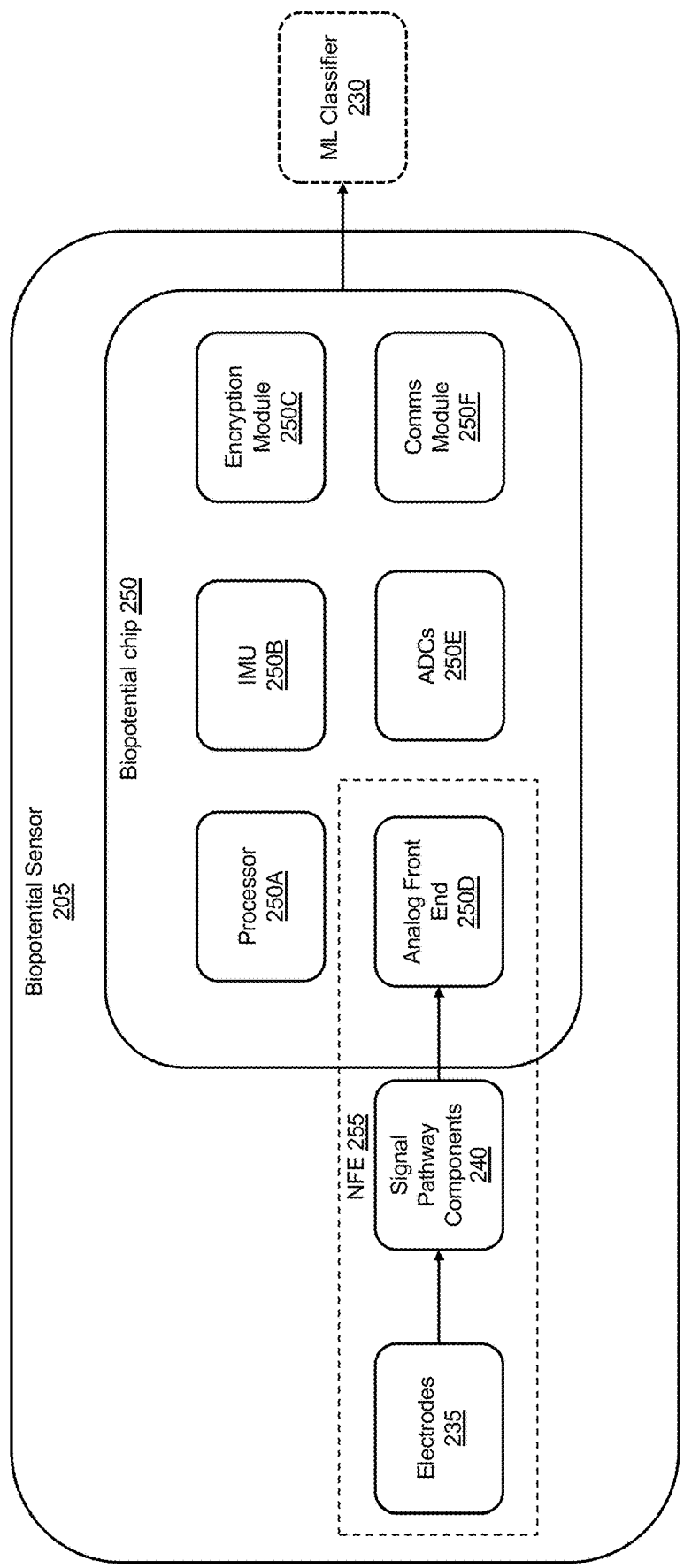
Figure 2C:
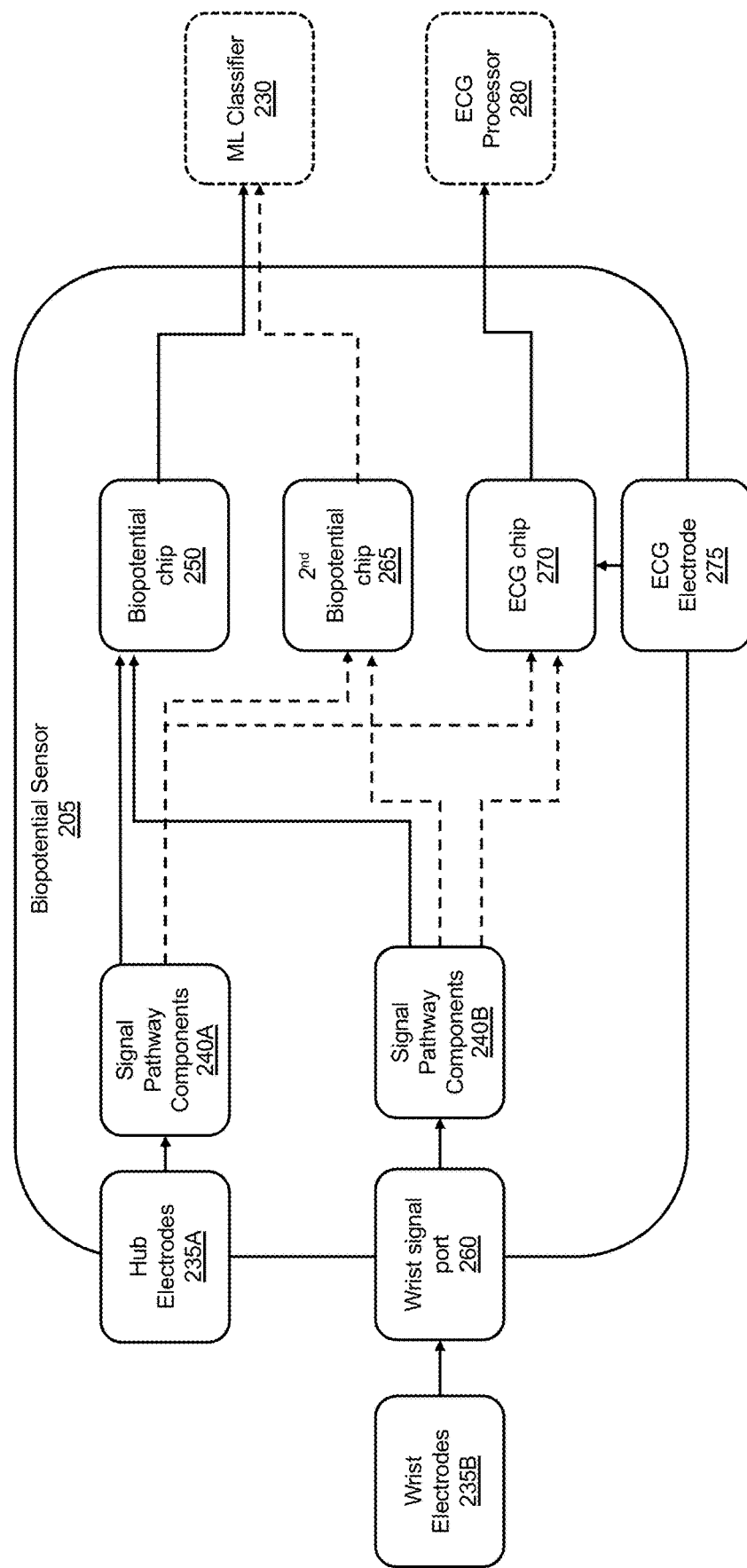

FIGS. 2A-2C depict block diagrams 200A, 200B, and 200C of aspects of a wearable device 110. The aspects of the wearable device 110 in block diagrams 200A, 200B, and 200C may apply to the wearable device 110, as discussed in FIG. 1 above.

In FIG. 2A, diagram 200A may depict a biopotential sensor 205, a central processing unit 210 ("CPU 210"), a memory 215, a display/user interface 220 ("UI 220"), a haptic feedback module 225 (e.g., a vibration motor), and a machine learning classifier 230 ("ML classifier 230") in a wearable device 110.

The biopotential sensor 205 may detect gesture data (e.g., biopotential signals, acceleration data, and/or orientation data of a portion of a user's arm). In some cases, the biopotential chip 250 may have the ML classifier 230 onboard and the biopotential chip 250 may provide the gesture data to the ML classifier 230, so that the ML classifier 230 may generate a gesture output indicating a gesture performed by the user 105. In some cases, the biopotential chip 250 may relay the gesture data to the ML classifier 230 (e.g., in the CPU 210 or outside the wearable device 110, such as in the user device 115, a local device 120, and/or the server 130). Further details of the biopotential sensor 205 are discussed herein.

The memory 215 may store instructions (e.g., software code) for an operating system (e.g., a wearable device O/S) and at least one application, such as a biopotential sensor application. The memory 215 may also store data for the wearable device 110, such as user data, configurations of settings, and the like, but also biopotential sensor data. The biopotential sensor data may include various bits of data, such as raw biopotential data for gesture data, processed gesture data, gesture outputs, user feedback for the same, and the like.

The CPU 210 may execute the instructions to execute the O/S and the at least the biopotential sensor application. The 0/S may control certain functions, such as interactions with the user 105 via the UI 220 and/or the haptic feedback 225. The UI 220 may include a touch display, display, a microphone, a speaker, and/or software or hardware buttons, switches, dials, and the like. The haptic feedback 225 may be an actuator to cause movement of the wearable device 110 (e.g., a vibration and the like) to indicate certain states or data. The CPU 210 may also include a communication module to send and receive communications to, e.g., the server 130, the user device 115, and/or the local device(s) 120.

The biopotential sensor application, via the CPU 210, may also interact with the user via the UI 220 and/or the haptic feedback 225. In some cases, the biopotential sensor application, via the CPU 210, may send and receive communications to, e.g., the server 130, the user device 115, and/or the local device(s) 120. In some cases, the biopotential sensor application, via the CPU 210, may instruct the biopotential sensor 205 to change connection states, such as from gesture detection mode to ECG detection mode, and the like, as discussed herein. In some cases, the biopotential sensor application, via the CPU 210, may interface between the biopotential sensor 205 and the O/S.

The ML classifier 230 may, based on the gesture data, generate the gesture output indicating the gesture performed by the user 105. As discussed above, the ML classifier 230 may be hosted on the wearable device 110, the user device 115, or the server 130. Generally, the ML classifier 230 may be a trained ML model to classify a gesture based on one or more of biopotential signals, acceleration data, and/or orientation data of a portion of a user's arm). For instance, the ML classifier 230 may be trained on a training dataset (e.g., gesture data and/or labels) in a supervised, an unsupervised, or semi-supervised manner. In some cases, the ML classifier 230 may output a result set of gestures with confidence values, and select a gesture with a highest confidence value as an identified gesture. In some cases, the ML classifier 230 may only identify a gesture if a confidence value is above a threshold. Further details for ML classification of gestures may be found in U.S. Pat. Nos. 10,070,799, 10,802,598, 11,199,908, and 11,157,086, and U.S. patent application Ser. Nos. 16/196,462, 16/774,825, and 16/737,252, each of which is incorporated by reference herein in its entirety. For instance, the gestures may include: index finger lift, index finger lift-and-hold, index finger swipe, thumbs up, wrist roll (e.g., palm open, first closed, index finger or thumb extended), wrist shake, and others.

In FIG. 2B, diagram 200B shows a first embodiment of the biopotential sensor 205. In this case, the biopotential sensor 205 may include a biopotential chip 250 and a neural front end 255 ("NFE 255"). The NFE 255 may include an analog front end 250D of the biopotential chip 250 and electrodes 235 and signal pathway components 240 off of the biopotential chip 250. The biopotential chip 250 may include a processor 250A, an inertial measurement unit 250B ("IMU 250B"), an encryption module 250C, the analog front end 250D, analog-to-digital converters 250E ("ADCs 250E"), and a communications module 250F ("comms module 250F"). The biopotential chip 250 may be manufactured as an integral unit and have all of the processor 250A, the IMU 250B, the encryption module 250C, the analog front end 250D, the ADCs 250E, and the communications module 250F located on a common unitary substrate.

The electrodes 235 may each be metal configured to contact a portion of skin to detect a biopotential signal. For instance, the electrodes 235 may include a plurality of electrodes 235 disposed on an interior of the wearable device 110 and configured to obtain biopotential signals from the user's arm. In some cases, the electrodes 235 may be a solid metal electrode with a face of various shapes, e.g., a polygon, a square, a circle, an arc segment, a circle sector (with or without extending to a center of the circle), and the like. The face may be configured to contact the portion of the skin. The face may be flat or curved (e.g., a dome of a certain radius). The solid metal electrode may be made of stainless steel, and the like. The solid metal electrode may extend from the face for a given length. In some cases, the solid metal electrode may include a threaded portion to engage a first retention member that has a corresponding opposite threaded portion. In some cases, the solid metal electrode may include a pressure fit portion that engages a second retention member that pressure fit holds the solid metal electrode via the pressure fit portion. In some cases, the first or second retention member may retain the solid metal electrode to a housing (e.g., of a wristband electrode) or a housing of a hub. In some cases, the solid metal electrode may be an "active electrode" that buffers biopotential signals. In this case, the solid metal electrode may also include a printed circuit board (PCB) and signal pathway components 240 for active buffering of the biopotential signal (hereinafter "buffer components"). For instance, the buffer components may include one or combinations of an amplifier, a capacitor, a power source, a filter, and the like.

In some cases (e.g., on a wristband), the electrodes 235 may be metal filament grouped in certain arrangements. For instance, the metal filament may be sewn into (e.g., in the case of a textile) or placed onto (e.g., in the case of a rubber or other material) an interior face of a wristband into various shapes, e.g., a polygon, a square, a circle, an arc segment, a circle sector (with or without extending to a center of the circle), and the like. In some cases, the metal filament electrode may be an "active electrode" that buffers biopotential signals. In this case, the metal filament electrode may be connected to a PCB and buffer components for active buffering of the biopotential signal. The metal filament electrode may be proximately located to the PCB and buffer components, such as on a housing protecting the PCB and buffer components, or on an opposite side of a wristband from the housing with the PCB and buffer components. In some cases, the housing for the PCB and buffer components may be attached to the wristband, embedded in the wristband, surround the wristband, or separate and re-connected the wristband, and the like. In some cases, the housing may be a rigid material (e.g., rubber or plastic). In some cases, the housing may be a laminate or shielded textile.

In some cases, the wearable device 110 is a smartwatch and the plurality of electrodes 235 are disposed in a circular arrangement on an inner surface of a hub of the smartwatch. In this case, the plurality of electrodes 235 may be configured to contact a top of the user's arm when the smartwatch is worn. In some cases, the biopotential chip 250 may be disposed in the hub of the smartwatch. In some cases, at least one of the plurality of electrodes 235 is a wristband electrode. The wristband electrode may be disposed on an interior surface of a wristband of the smartwatch. The wristband electrode may be configured to contact a portion of the user's arm different than the top of the user's arm when the smartwatch is worn. The wristband electrode may be electrically coupled to the biopotential chip 250 disposed in the hub of the smartwatch.

The signal pathway components 240 may include electrical conductors (e.g., metal wires that are insulated or not), traces, and the like. In some cases, the signal pathway components 240 may include switches to change signal pathways of biopotential signals.

The analog front end 250D (see, generally, FIGS. 3A-3C) may include a plurality of analog inputs 305 (see FIG. 3A) configured to be coupled to and receive the biopotential signals from the plurality of electrodes 235. In some cases, one or more of the plurality of analog inputs 305 may be coupled to respective differential amplifiers 315 (see FIG. 3A). The differential amplifiers 315 may be configured to amplify differences in signals between pairs of electrodes.

The ADCs 250E may include a plurality of ADCs. The ADCs 250E may be configured to convert the biopotential signals to biopotential data. For instance, the ADCs 250E may be connected to outputs of corresponding differential amplifiers 315 and may convert the differential signals to biopotential data.

The IMU 250B may be disposed onboard the biopotential chip 250. The IMU 250B may include at least an accelerometer and a gyroscope. The accelerometer may output acceleration data of a portion of a user's arm and the gyroscope may output orientation data (e.g., an angular position or angular rate) of a portion of a user's arm.

The processor 250A may be configured to process the biopotential data outputted by the ADCs 250E, the acceleration data outputted by the accelerometer of the IMU 250B, and/or the orientation data outputted by the gyroscope of the IMU 250B (collectively, "initial gesture data"). For instance, the processor 250A may time sync the initial gesture data, format the initial gesture data for transmission, and send the initial gesture data (as processed into gesture data) to the comms module 250F.

In some cases, the processor 250A may encrypt the initial gesture data using the encryption module 250C. For instance, to encrypt the initial gesture data, using the encryption module 250C, the encryption module 250C may store (and, optionally generate) a private biopotential key and a public biopotential key, and store one or more external public keys corresponding to the ML classifier, the CPU 210, the device 115, or the server 130. The processor 250A (or the encryption module 250C) may retrieve the private biopotential key and an external public key corresponding to a destination (e.g., the ML classifier, the CPU 210, the device 115, or the server 130), and encrypt the initial gesture data using the private biopotential key and an external public key. The processor 250A may transmit, e.g., separately or in a same packet or a first packet), the public biopotential key to one or more of the ML classifier, the CPU 210, the device 115, or the server 130 (referred to as "endpoint"). The endpoint may store the public biopotential key. The endpoint may have a corresponding private key to the external public key. The endpoint may transmit the public key to the processor 250A, so that the processor 250A may store it in encryption module 250C. The endpoint may use the public biopotential key and its private key to decrypt any encrypted gesture data received from the biopotential chip.

In some cases, the processor 250A may normalize the initial gesture data. For instance, to normalize the initial gesture data, the processor 250A may map the initial gesture data into a defined range of values based on data type. In some cases, the biopotential data outputted by the ADCs 250E may be scaled (e.g., proportionally in accordance with the values of the biopotential data with respect to a maximum biopotential signal value) between a first value (e.g., 0) and a second value (e.g., 1 or 100, and the like), In some cases, the acceleration data outputted by the accelerometer of the IMU 250B may be scaled (e.g., proportionally in accordance with the values of the acceleration data with respect to a maximum acceleration value) between a first value (e.g., −1) and a second value (e.g., 1). In some cases, the orientation data outputted by the gyroscope of the IMU 250B may be scaled if the orientation data includes rates of change (e.g., rotational velocity or rotational acceleration) of orientation between a first value (e.g., 0) and a second value (e.g., 1 or 100, and the like). By normalizing the initial gesture data using the processor 250A of the biopotential chip, the initial gesture data may be better formatted for analysis by a classifier.

The comms module 250F may then transmit the gesture data to the ML classifier 230, whether the ML classifier is onboard the wearable device 110, the user device 115, or the server 130. For instance, the comms module 250F may transmit the gesture data to the CPU 210, so that the CPU 210 may process it (e.g., via the biopotential application) or transmit the gesture data to the user device 115 or the server 130.

In some cases, the processor 250A may control connection states between electrodes 235 and biopotential chips, an ECG chip 270, or specific differential amplifiers within biopotential chips, as discussed herein. In these cases, the processor 250A may cause switches or a multiplexer to change signal pathways from form a currently active connection state (for a first mode) to a new active connection state (for a second mode). For instance, the connection states may correspond to various modes, such as a biopotential sensing mode, a training mode, an ECG detection mode, right arm mode, left arm mode, an impendence measurement mode, and the like.

In some cases, the switches or multiplexer may be configured to apply a plurality of connection states between the plurality of electrodes 235 and the differential amplifiers (of a same or a different biopotential chip) or analog inputs of an ECG chip. For instance, in some cases, the switches or multiplexer may apply a first connection state in which a first pair of electrodes of the plurality of electrodes 235 is connected to a first differential amplifier. The first differential amplifier may be configured to amplify a difference in signals obtained by the first pair of electrodes in the first connection state. The switches or the multiplexer may then apply a second connection state in which a second pair of electrodes of the plurality of electrodes 235 is connected to the first differential amplifier, and the first differential amplifier may be configured to amplify a difference in signals obtained by the second pair of electrodes in the second connection state. In some cases, at least one of the electrodes of the second pair of electrodes is not included in the first pair of electrodes.

In FIG. 2C, diagram 200C shows a second embodiment of the biopotential sensor 205. In this case, the biopotential sensor 205 may include the biopotential chip 250 with at least one other biopotential chip, such as second biopotential chip 265, and an ECG chip 270. In some cases, the biopotential sensor 205 may be connected to different sets of electrodes 235, such as hub electrodes 235A and wristband electrodes 235B. In some cases, the hub electrodes 235A may have signal pathway components 240A that are the same or different than signal pathway components 240B for the wristband electrodes 235B. For instance, the signal pathway components 240B for the wristband electrodes 235B may be located proximate the wristband electrodes 235B (e.g., outside a housing of the biopotential sensor 205 and on a wristband). As the wristband electrodes 235B may be outside the housing of the biopotential sensor 205, the signal pathway for biopotential signals from the wristband electrodes 235B may pass through a wrist signal port 260.

In some cases, the biopotential signals from the hub electrodes 235A and the wristband electrodes 235B may be routed to a same or different biopotential chip, or switched between biopotential chips. For instance, due to form factor and/or chip sizing constraints, different (e.g., pairings of) biopotential signals may be processed on different biopotential chips. In some cases, the biopotential chips may process the biopotential signals differently. Generally, the processor 250A may instruct switches or a multiplexer to route certain biopotential signals to certain biopotential chips (or certain differential amplifiers of a biopotential chip) by changing a connection state between electrodes 235 and biopotential chips (or differential amplifiers of a biopotential chip).

In some cases, the hub electrodes 235A and the wristband electrodes 235B may be connected to the biopotential chip 250 in a first connection state (e.g., by switches or a multiplexer), and the hub electrodes 235A and the wristband electrodes 235B may be connected to the second biopotential chip 265 in a second connection state (e.g., by switches or a multiplexer). For instance, the switches or multiplexer may be controlled by the processor 250A to change the connection state between the first connection state (for a first mode, such as biopotential sensing mode) and the second connection state (for a second mode, such as a training mode).

In some cases, the hub electrodes 235A may be connected to the biopotential chip 250, while the wristband electrodes 235B may be connected to the second biopotential chip 265 (or vice versa). In some cases, a first subset the hub electrodes 235A may be connected to the biopotential chip 250, a first subset the wristband electrodes 235B may be connected to the biopotential chip 250, a second subset the hub electrodes 235A may be connected to the second biopotential chip 265, and a second subset the wristband electrodes 235B may be connected to the second biopotential chip 265.

In some cases, all (or subsets of) the hub electrodes 235A and the wristband electrodes 235B may be selectively connected (e.g., by switches or a multiplexer, in a third connection state) to the ECG chip 270. The ECG chip 270 may also be connected to an ECG electrode 275, which may be different from the hub electrodes 235A and wristband electrodes 235B and located on the biopotential sensor such that the ECG electrode 275 would not ordinarily contact the wrist of the person. For instance, the switches or multiplexer may be controlled by the processor 250A to change the connection state between the first connection state or the second connection state to the third connection state. For example, a processor of the biopotential sensor 205 may detect that a user has contacted the ECG electrode (e.g., with one or more fingers of the hand opposite the arm on which the biopotential sensor 205 is worn), and in response to determining that the user has contacted the ECG electrode, the system may switch the signal pathway components for the hub electrodes and/or wristband electrodes such that at least some of the signals from these electrodes are directed to the ECG chip 270.

The ECG chip 270 may process the biopotential signals from all (or subsets of) the hub electrodes 235A and the wristband electrodes 235B and the biopotential signal from the ECG electrode 275, and generate ECG data. The ECG data may be a digital signal based on the biopotential signals. The ECG chip 270 may transmit the ECG data to an ECG processor 280. The ECG processor 280 may receive the ECG data and produce an electrocardiogram based on the ECG data. For instance, the ECG chip 270 (to generate the ECG data, or the ECG processor 280 based on the digital signal) may filter power line interference (e.g., 60 Hz in the US), and measure frequency of cardiac pulses (e.g., heart rates). For instance, cardiac pulses of a cardiac signal may have three (3) primary structures, that are areas of a waveform for the cardiac signal. In some cases, the ECG chip 270 may detect the primary structures and compare magnitudes and relative magnitudes of the detected primary structures. In some cases, the ECG chip 270 may cause an alert to be transmitted or output (e.g., to the user or a Doctor) about certain detected cardiac anomalies indicated by comparisons of the magnitudes and relative magnitudes of the detected primary structures. The ECG processor 280 may be a part of the wearable device 110 (e.g., be hosted on the CPU 210 or separate from the CPU 210) or on a different device, such as the user device 115 or the server 130.

In some cases, the second biopotential chip 265 may include some or all of the same features as the biopotential chip 250. In some cases, the second biopotential chip 265 may include the IMU 250B and the IMU 250B may be omitted from the biopotential chip 250.

In some cases, the processor 250A of the biopotential chip 250 or the biopotential application, executed by the CPU 210, (or a different device, such as the user device 115 or the server 130) may determine that an impedance determination check is to be performed. For instance, the CPU 210 or the processor 250A of biopotential chip 250 may determine that the impedance determination check is to be performed in response to an impedance check timer elapsing (e.g., for inter or intra-session wearing), in response to a recalibration process being conducted, or in response certain signal characteristics changing over time. For instance, the biopotential chip 250 may detect presence of significant (e.g., higher than a threshold value) amount of interference (e.g., electrical line frequency, e.g., 60 Hz in the US) in the biopotential signals. The presence high interference may be indicative of poor electrode-skin contact, that is high impedance. The detection of the interference may be performed in parallel to gesture classification continuously, or periodically (e.g., depending upon implementation considerations, such as space, volume, electrical power draw, and/or component cost). In some cases, detecting interference (instead of, e.g., only periodically switching to impendence measurement) may avoid interrupting gesture classification, whereas switching to impendence measurement periodically may interrupt the gesture classification. In this case, user convenience may be maintained for gesture classification. In response to this determination, an impedance command may be transmitted (e.g., from the CPU 210, the user device 115, or the server 130) to the processor 250A (or the processor 250A may have determined to perform the impedance check). The processor 250A may then cause a connection state change by changing a state of switches or the multiplexer so as to connect certain electrodes to certain points, such as to an impedance processing circuit of the first or second the second biopotential chips (if configured to perform impedance measurements).

For instance, in an impedance measurement mode, the processor 250A may connect a stimulus source to at least one first electrode (e.g., a first electrode) of the plurality of electrodes 235, and connect the at least one first electrode and at least one second electrode of the plurality of electrodes 235 to an impedance processing circuit of the first or second biopotential chips, so that electrical signals from the at least one first electrode and at least one second electrode may be carried to the impedance processing circuit. The stimulus source may then apply a stimulus to the at least one first electrode, and the biopotential chip may receive corresponding electrical signals. The second biopotential chip 265 may analyze the electrical signals from the at least one first electrode and the least one second electrode to determine an impedance measurement signal. The impedance measurement signal may include a response to the stimulus applied to the at least one first electrode. The biopotential chip may, based on the impedance measurement signal, determine an impedance between the at least one first electrode and the at least one second electrode.

The chip may output the determined impedance between the at least one first electrode and the at least one second electrode to the processor 250A, and the processor 250A (or CPU 210, or another device, such as user device 115 or server 130) may determine whether the signal quality is impaired. For instance, the signal quality may be impaired if the determined impedance between the at least one first electrode and the at least one second electrode satisfied an impairment condition (e.g., is greater than a first threshold or less than a second threshold). In some cases, based on the determined impedance between the at least one first electrode and the at least one second electrode and/or the impairment condition being satisfied, the wearable device 110 (or the user device 115) may present to the user 105 an indication that signal quality is impaired. For instance, the indication may be a haptic feedback, an audio noise, a display graphic, and the like. In some embodiments, the impedance measurement, or derivative thereof, may be provided to the ML classifier 230 and used as an input for gesture determination. For example, the ML classifier may be trained to apply higher confidence or to make gesture classifications more quickly, based on less data, or based on smaller signal deviations when it is determined that impedance measurements indicate high contact quality. In some case, the impendence measurements may be an input to the ML classifier. For example, an impendence measurements may be periodically or simultaneously obtained with gesture data (e.g., EMG and wrist motion data), and the multiple data sources may analyzed by the ML classifier to determine gesture classifications and/or to modify confidence rating or others parameters relating to classifications or confidences.

The biopotential chip 250 may have a first low-power state and an active state. In some cases, the first low-power state may turn off (e.g., not enable, not provide power to) at least the ADCs 250E and the differential amplifiers 315 and turn on (e.g., enable, provide power to) the accelerometer and the gyroscope. In some cases, the active state may turn on (e.g., enable, provide power to) the ADCs 250E, the differential amplifiers 315, the accelerometer, and the gyroscope. The biopotential chip 250 may be configured to transition from the first low-power state to the active state in response to an activate command. In some cases, the biopotential chip 250 may determine the activate command be based on detecting certain acceleration and/or orientation data while in the first lower-power state. In some cases, the activate command may be generated externally from the biopotential chip 250 (e.g., from the user device 115 or the server 130), and the biopotential chip 250 may receive activate command, via the CPU 210. In response to determining (or receiving) the activate command in the first low-power state, the biopotential chip 250 may turn on (e.g., enable, provide power to) the ADCs 250E and the differential amplifiers 315.

In some cases, the biopotential chip 250 may have a second low-power state. The second low-power state may turn off (e.g., not enable, not provide power to) at least the accelerometer and the gyroscope and turn on (e.g., enable, provide power to) the ADCs 250E and/or the differential amplifiers 315. In this case, the biopotential chip 250 may determine the activate command be based on detecting a certain gesture or combination of gestures. In response to determining (or receiving) the activate command in the second low-power state, the biopotential chip 250 may turn on (e.g., enable, provide power to) the accelerometer and the gyroscope.

Figure 3A:
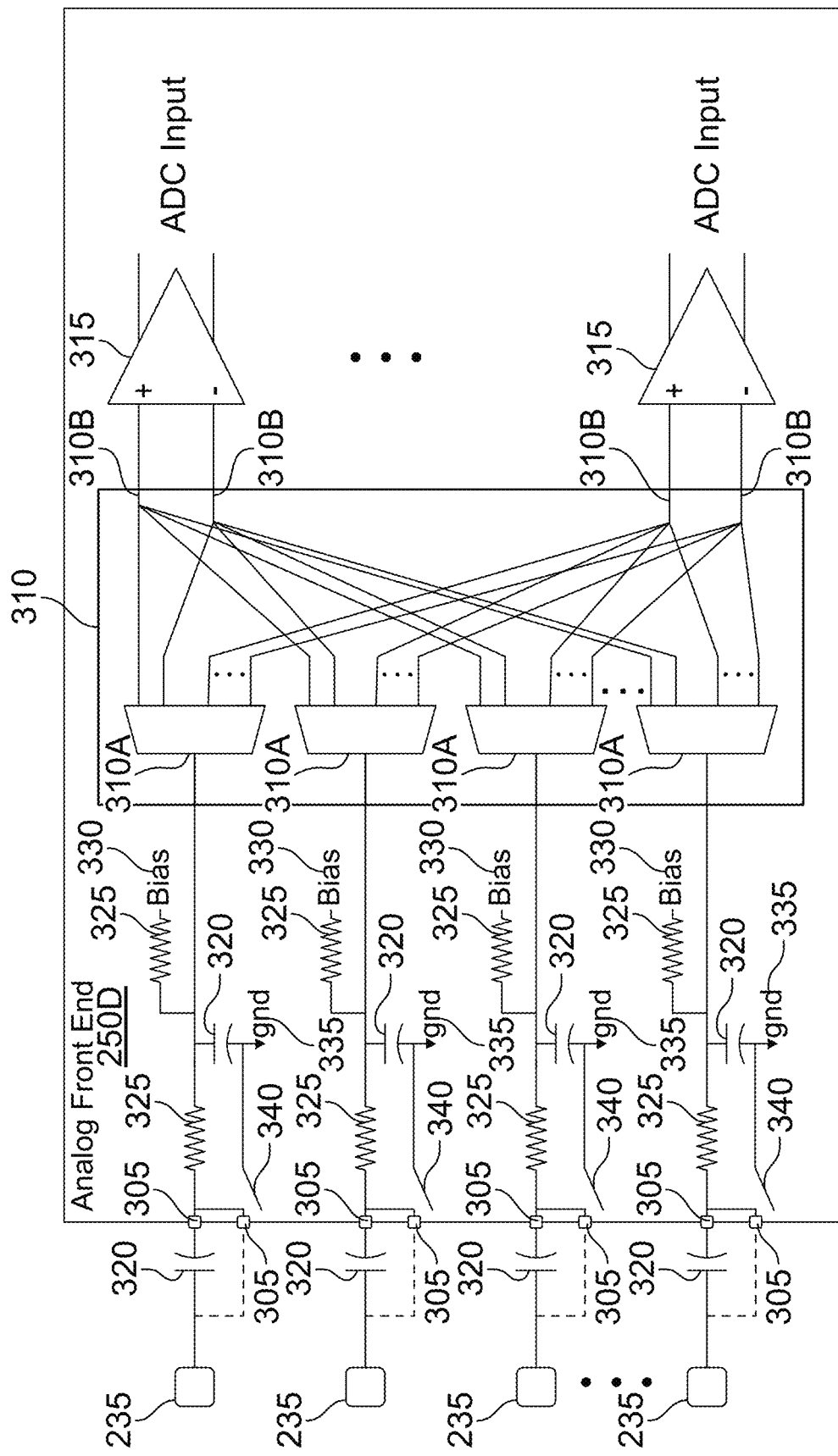
FIGS. 3A-3C depict schematic diagrams of aspects of a biopotential sensor of a wearable device.
Figure 3B:
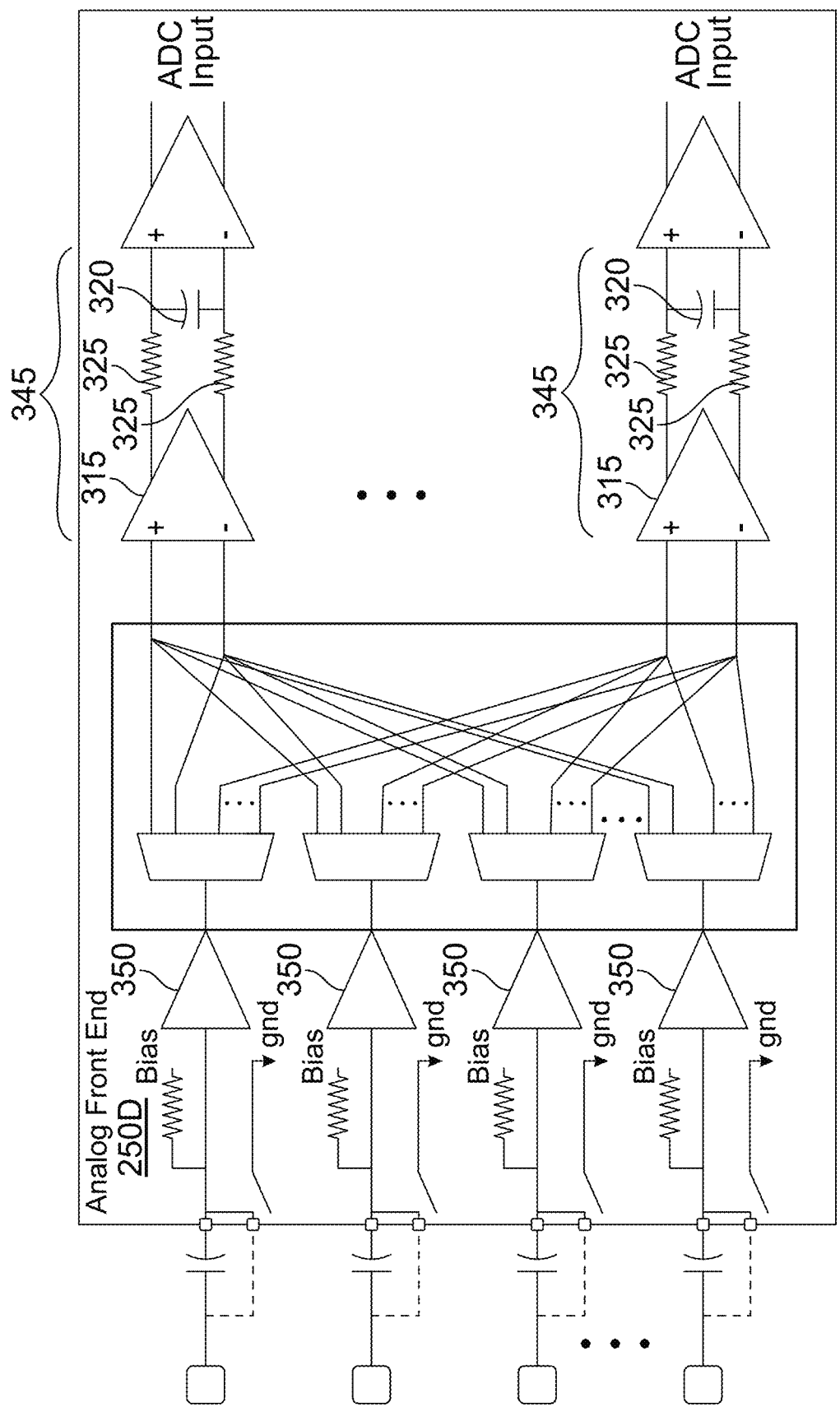
Figure 3C:
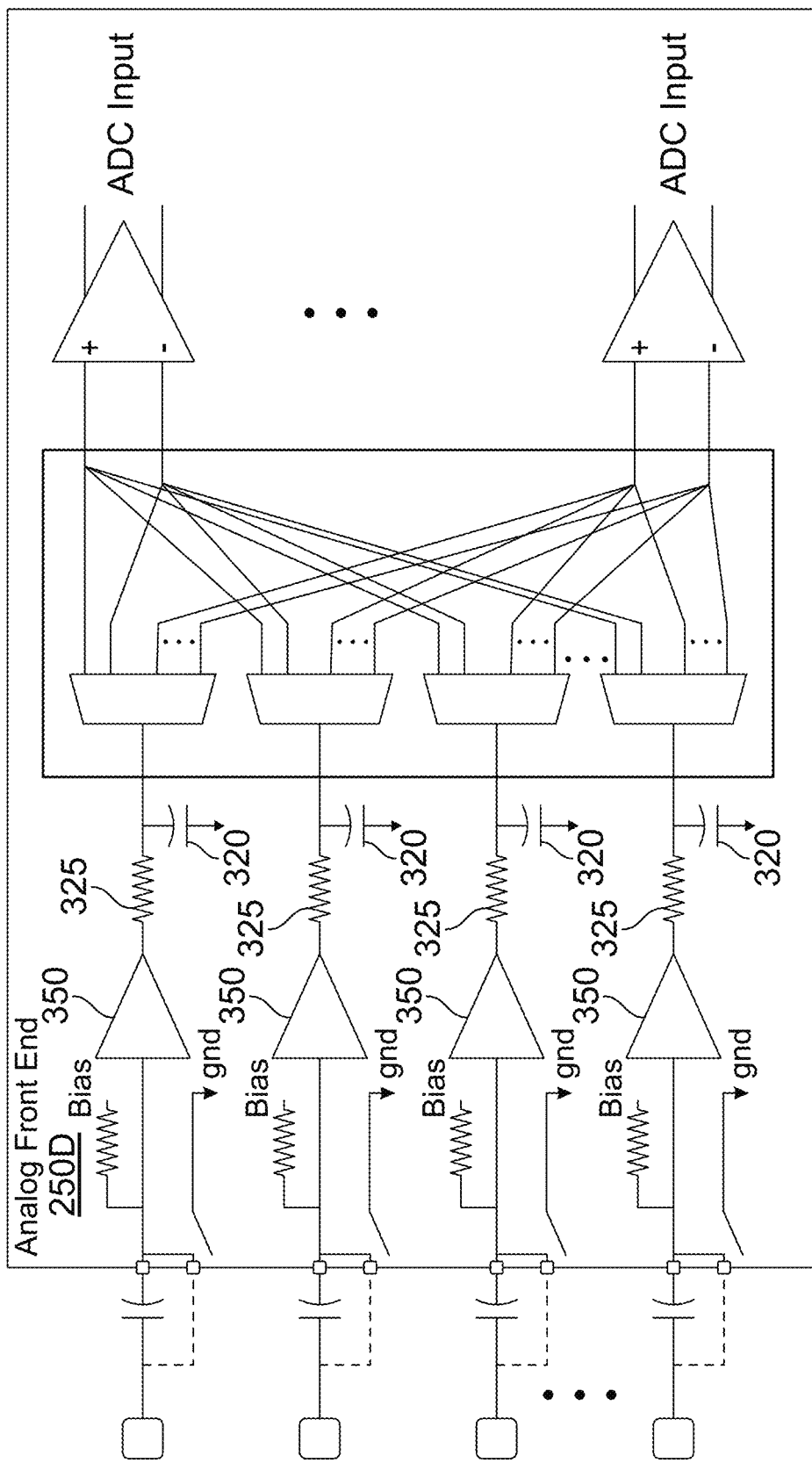

FIGS. 3A-3C depict schematic diagrams 300A, 300B, and 300C of aspects of a biopotential sensor 205 of a wearable device 110. The aspects of the biopotential sensor 205 of the wearable device 110 in block diagrams 300A, 300B, and 300C may apply to the wearable device 110, as discussed in FIGS. 1 and 2A-2C above. Diagrams 300A, 300B, and 300C may be modified to have different arrangements and include less or more components as shown.

In FIG. 3A, diagram 300A may depict a first arrangement aspects of the electrodes 235 (which may be hub electrodes or wristband electrodes), the signal pathway components 240, and the analog front end 250D. For instance, in diagram 300A, each electrode 235 may be connected to an analog inputs 305 of the analog front end 250D. In some cases, the signal pathway components 240 may include signal conductors (e.g., wires and/or traces) and other elements, such as a capacitor 320. In some cases, the signal pathway components 240 may include only the signal conductors. In some cases, none, some, or all of the electrodes 235 may have a second analog input 305 that (based on control of a switch 340 on the analog front end 250D) shorts the signal pathway to a ground 335. In some cases, the switch 340 may connect on a first side or a second side of the capacitor 320.

On the analog front end 250D, the analog front end 250D may include at least the plurality of differential amplifiers 315. Each of the differential amplifiers 315 may be coupled (or couplable) to a first electrode and a second electrode at a first input and a second input, respectively.

In some cases, the analog front end 250D may also include a multiplexer 310. The multiplexer may include a plurality of signal muxes 310A and a plurality of connection points 310B. For instance, each analog input 305 may correspond a signal mux 310A. The signal mux 310A may connect its respective analog input 305 to one (or more) of a set of connection points 310B. For instance, the set of connection points 310B may include some or all of the plurality of connection points 310B. Thus, each electrode 235 connected to an analog input 305 may be connected to first input or a second input of some or all of the differential amplifiers 315, thereby enabling the biopotential sensor 205 to change a sensed biopotential data.

In some cases, the multiplexer 310 may also change a signal pathway for an analog input 305 to a certain analog input 305 on a different biopotential chip (e.g., the biopotential chip 265) or an analog input 305 on the ECG chip 270. In this case, the multiplexer 310 may include additional connection points 310B so that the signal muxes 310A may connect the electrodes 235 to, via the analog input 305 of the analog front end 250D, to an analog input 305 on a different biopotential chip (e.g., the biopotential chip 265) or an analog input 305 on the ECG chip 270.

The analog front end 250D may also include various arrangements of analog filter(s) that include resistors 325, a bias 330, capacitors 320, and/or the ground 335. The elements of the analog filter(s) may be omitted or included, and, if included, may be arranged in various different arrangements to perform a filtering function. For instance, first analog filters may be in between the analog input 305 and the differential amplifiers 315. For instance, in diagram 300A, the first analog filters may be in between the analog input 305 and the signal muxes 310A of the multiplexer 310.

In FIG. 3B, diagram 300B may depict a second arrangement aspects of the electrodes 235, the signal pathway components 240, and the analog front end 250D. The second arrangement may be the same as the first arrangement, but also include a plurality of amplifiers 350 and a plurality of second analog filters 345. In some cases, the amplifiers 350 may be in between the analog inputs 305 and second analog filters 345. In some cases, the amplifiers 350 may be in between the analog inputs 305 and the multiplexer 310 with the second analog filters 345 arranged in between the multiplexer 310 and the differential amplifiers 315. The amplifiers 350 may amplify a signal received by an analog input 305. The second analog filters 345 may include a differential amplifier 315 coupled in series to a pair of resistors 325 and a capacitor 320.

In FIG. 3C, diagram 300C may depict a third arrangement aspects of the electrodes 235, the signal pathway components 240, and the analog front end 250D. The third arrangement may be the same as the first arrangement, but also include a plurality of amplifiers 350 (like in the second arrangement), with third second analog filters with resistors 325 and capacitors 320 in between the amplifiers 350 and the differential amplifiers 315 (e.g., before the multiplexer 310).

In general, including capacitors 320 and/or resistors 325 in the first, second, or third analog filters may regulate the biopotential signal for signal quality. In some cases, a capacitor 320 may make the system less vulnerable to DC shifts (of the biopotential signal) than if directly coupled. In some cases, an electrode may become charged due to polarization, and the effect of the polarization may be lessened by the capacitor 320. In some cases, the resistor 325 may lessen the effect of voltage read changing due to skin impedance changing. That is to say, the skin may have a constantly shifting impedance, but if skin is in series with a large value resistor, the shifting values of skin resistance may contribute a relatively small amount (e.g., compared to the resistor 325) to the noise of the front end system. For instance, an effective resistance may be equal to the resistance of the skin and the resistance of the front end system, but if the resistance of the front end system is greater (e.g., 10×, 100×, and the like) than the resistance of the skin, the effective resistance is substantially the resistance of the resistance of the front end (and accounted for in design).

FIGS. 4A-4D depict graphics 400A, 400B, 400C, and 400D of different arrangements of hub electrodes 235A of a wearable device 110. The different arrangements of the hub electrodes 235A of the wearable device 110 in graphics 400A, 400B, 400C, and 400D may apply to the wearable device 110, as discussed in FIGS. 1, 2A-2C, and 3A-3C above. Graphics 400A, 400B, 400C, and 400D may be modified to have different arrangements and include less or more components as shown.

Figure 4A:
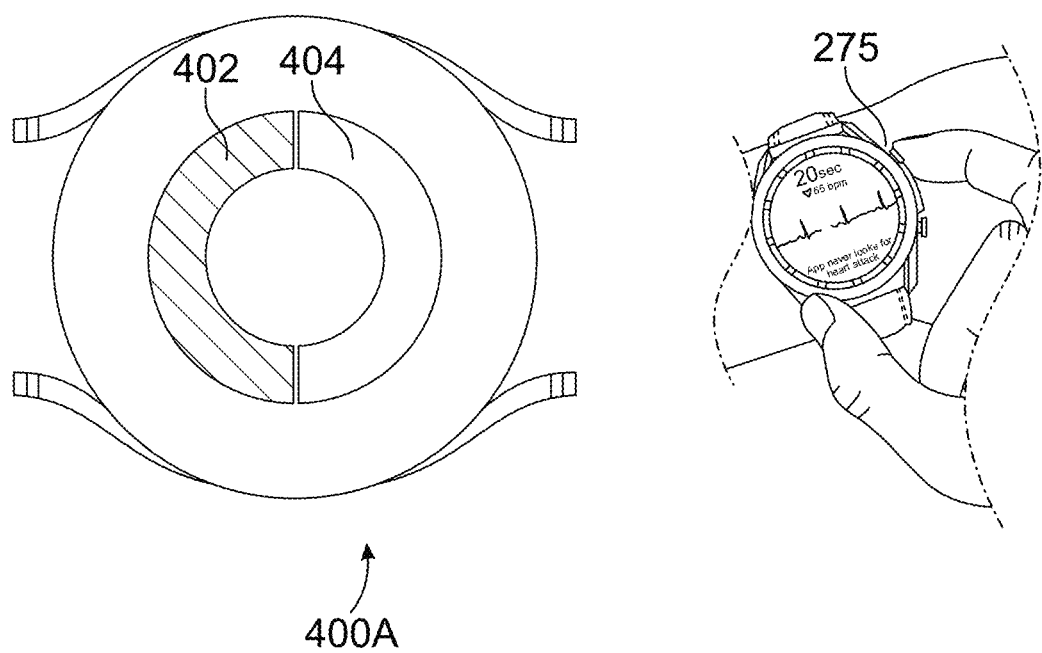

In FIG. 4A, graphic 400A may depict the ECG electrode 275 and a first arrangement (e.g., a pair) of hub electrodes 402 and 404. In some cases, a first hub electrode 402 or a second hub electrode 404 may be a reference electrode that inputs a biopotential signal to the ECG chip 270. For instance, the first hub electrode or the second hub electrode may be connected to a biopotential chip, such as the biopotential chip 250 or the second biopotential chip 265 in, e.g., the first or second connection state, and then connected to the ECG chip 270 in the third connection state. In some cases, the ECG electrode 275 is positioned on the wearable device 10 such that the ECG electrode 275 is not in contact with the user's arm when the wearable device 110 is being worn on the arm of the user 105. For instance, as depicted in FIG. 4A, the ECG electrode 275 is positioned on a side of the wearable device 110 and not in contact with the user's arm when the wearable device 110 is being worn. In some cases, the ECG electrode 275 may be positioned on other locations (not depicted), such as a top of the wearable device 110 or on a wristband (on an exterior facing surface of the wristband).

In some cases, the processor 250A may detect that the user 105 has contacted the ECG electrode 275; and in response to detecting that the user has contacted the ECG electrode, transition from a current connection state (e.g., the first connection state or the second connection state) to the third connection state. In this manner, hub electrodes 402 or 404 may provide dual functionality including at least biopotential sensing for gesture control and ECG sensing as a reference electrode, thereby increasing functionality while minimizing a number of sensor components that interact with users.

Figure 4B:
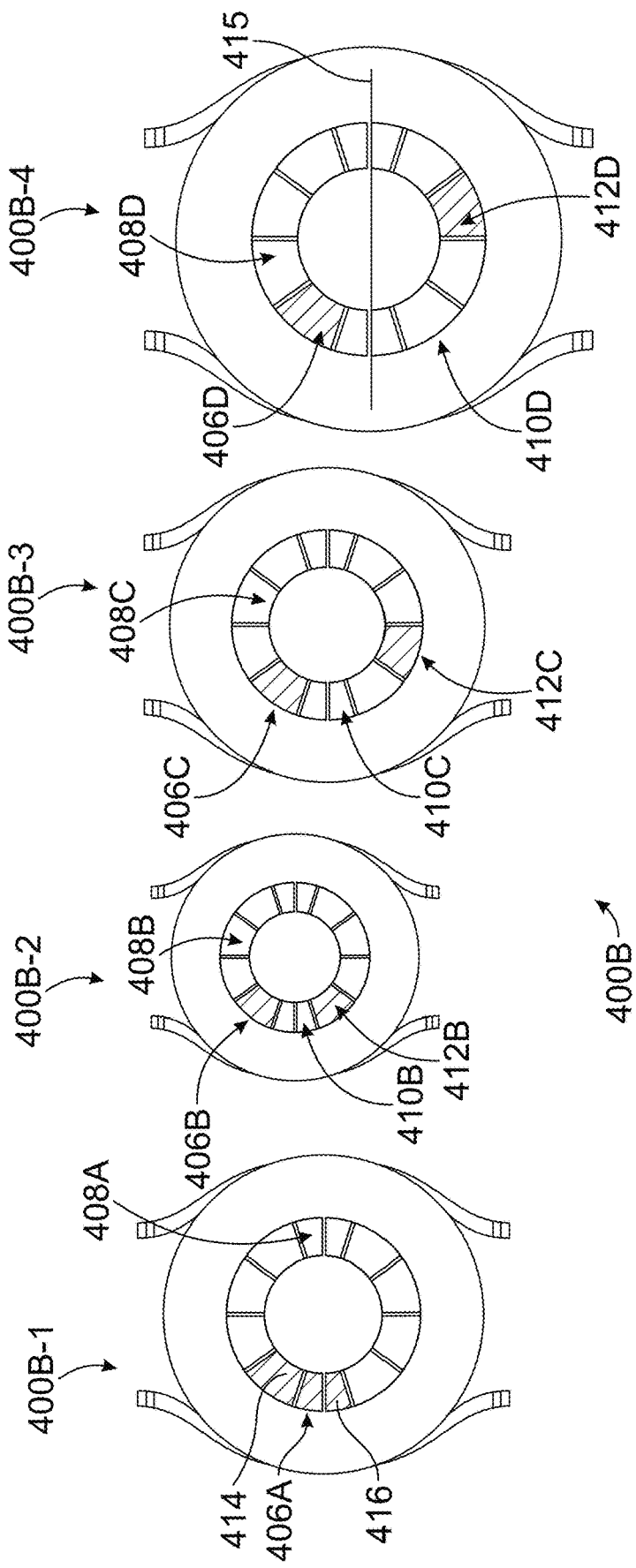

In FIG. 4B, graphic 400B may depict a second arrangement of the hub electrodes 235A. For instance, the hub electrodes 235A may be a plurality of circle sector electrodes that extend from an interior diameter to an exterior diameter. In some cases, the circle sector electrodes may be centered on a same center point (e.g., to surround the center point in a circular arrangement (e.g., a ring)). The circle sector electrodes may be uniform in arc length (see, e.g., FIG. 4C) or not uniform in arc length (see FIG. 4B or 4D). In FIG. 4B, the circle sector electrodes may include a first circle sector type 414 and a second circle sector type 416. The first circle sector type 414 may have a larger arc length then the second circle sector type 416. In some cases, the hub electrodes 235A may have a same or different number of the first circle sector type 414 as a number of the second circle sector type 416. For instance, as depicted in FIG. 4B, there may be eight electrodes of the first circle sector type 414 and four electrodes of the second circle sector type 416. In some cases, the arrangement of electrodes of the first circle sector type 414 and the second circle sector type 416 may be symmetrical along at least one axis 415.

In some cases, different sets of hub electrodes 235A may be used as reference inputs to the ECG chip 270 when in the third connection state. For instance, in graphic 400B-1, a first group 406A of hub electrodes 235A may be connected to the ECG chip 270 as reference electrodes, while a second group 408A may not be connected to the ECG chip 270, when in the third connection state. In this case, the first group 406A may form first continuous sequence of adjacent hub electrodes 235A, while the second group 408A may form a second continuous sequence of adjacent hub electrodes 235A. In other cases, such as in graphics 400B-2, 400B-3, or 400B-4, the first group 406B/406C/406D may not be adjacent third group 412B/412C/412D of reference electrodes, thereby being separated by the second group 408B/408C/408D and a fourth group 410B/410C/410D. The sequence length (e.g., a number of adjacent electrodes) for each group may be the same or different. For instance, in graphic 400B-2, the first group 406B (one electrode of first circle sector type 414) may be separated from the second group 412B (one electrode of first circle sector type 414) by the fourth group 410B (a double electrode of second circle sector type 416); in graphic 400B-3, the first group 406C (one electrode of first circle sector type 414) may be separated from the second group 412C (one electrode of first circle sector type 414) by the fourth group 410C (two electrodes of second circle sector type 416 and one electrode of first circle sector type 414); and in graphic 400B-4, the first group 406D (one electrode of first circle sector type 414) may be separated from the second group 412D (one electrode of first circle sector type 414) by the fourth group 410D (two electrodes of second circle sector type 416 and two electrodes of first circle sector type 414). Of note, as the fourth group is increased in number of electrodes (and if the first group and third group stay the same), the second group is decreased in number of electrodes. Thus, in this manner, different regions of skin may be used as a reference for the ECG chip 270. In some cases, the processor 250A may change the selection of reference electrodes for the ECG chip 270. In some cases, the processor 250A may have the selection of reference electrodes stored as a configuration that is preset.

Figure 4C:
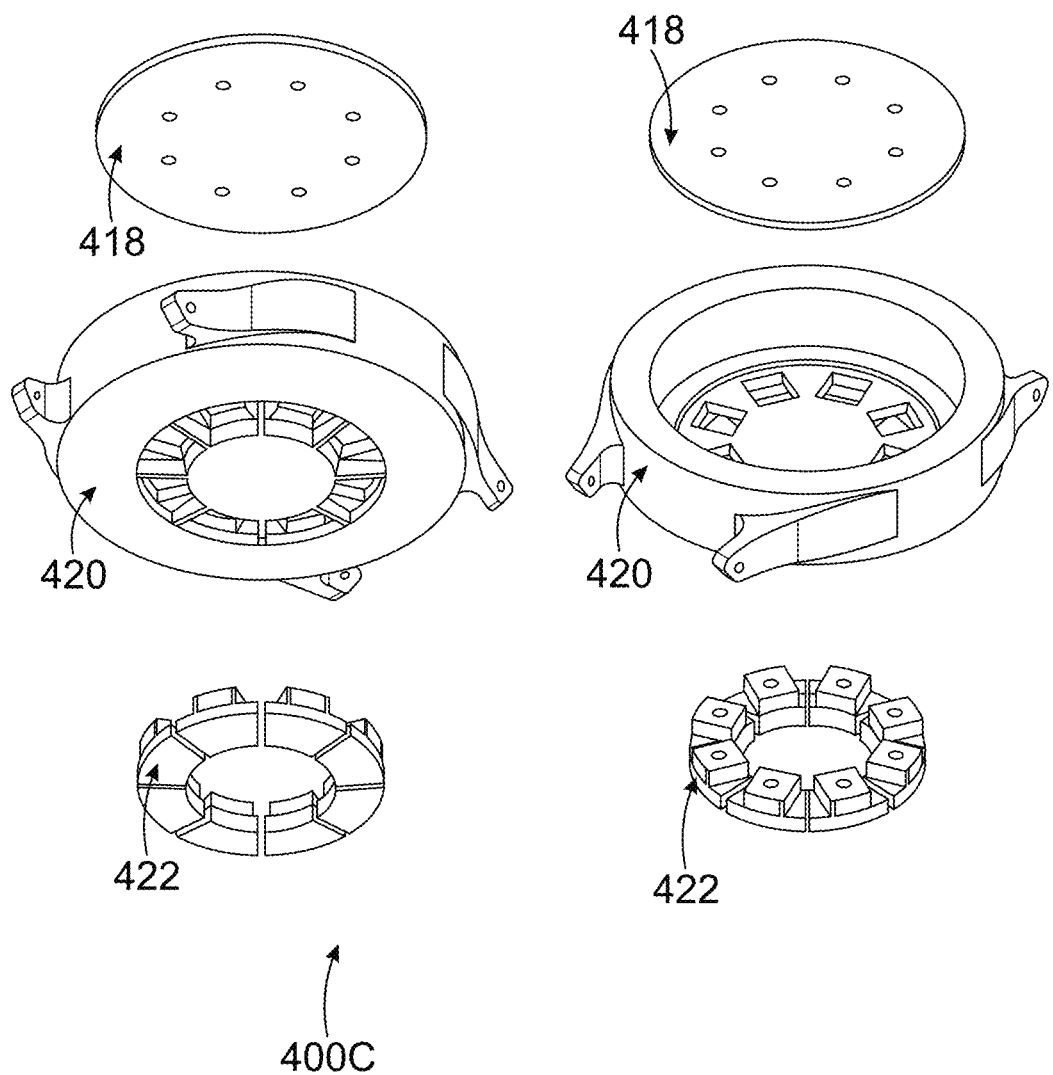

In FIG. 4C, graphic 400C may depict a third arrangement of circle sector electrodes 422 of a uniform arc length and depict how the circle sector electrodes 422 may be inserted into holes in a bottom 420 of a hub (or case) of the wearable device 110 and connected to a PCB 418. In some cases, the hub electrodes 235A of the first circle sector type 414 and the second circle sector type 416 may be inserted and connected in a similar manner. In some cases, the PCB 418 may be a disk to affix (e.g., via a first retention member) the circle sector electrodes 422 once inserted through the holes in the bottom 420. In some cases, the circle sector electrodes 422 may be affixed by the holes in the bottom via a second retention member (e.g., via pressure fit of the walls of the holes). The PCB 418 may include buffer components. The PCB 418 may carry biopotential signals to the analog inputs 305, via signal pathway components 240 (e.g., signal conductors and traces).

In FIG. 4D, graphic 400D may depict other arrangements of non-uniform arc length circle sector electrodes. In graphic 400D-1, a fourth arrangement 424 of hub electrodes 235A may include a third circle sector type 424A and a fourth circle sector type 424B. The third circle sector type 424A may have a longer arc length than the fourth circle sector type 424B. For instance, the third circle sector type 424A may have an arc length twice as long as the fourth circle sector type 424B, such that a single electrode of the third circle sector type 424A may have a same surface area as two electrodes of fourth circle sector type 424B. In some cases, the third circle sector type 424A may have an arc length corresponding to (or near to) 90° and the fourth circle sector type 424B may have an arc length corresponding to (or near to) 45°. The fourth arrangement 424 may, in sequence in a ring, proceed as follows: one electrode of the third circle sector type 424A, two electrodes of the fourth circle sector type 424B, one electrode of the third circle sector type 424A, and two electrodes of the fourth circle sector type 424B. In the graphic 400D-2, a fifth arrangement 426 may have a same arrangement as in the fourth arrangement, but one electrode of the third circle sector type 424A may be replaced by two electrodes of the fourth circle sector type 424B. In graphic 400D-3, a sixth arrangement 428 may have a same arrangement as the fifth arrangement, but the remaining electrode of the third circle sector type 424A and the adjacent electrodes of the fourth circle sector type 424B may be replaced by a fifth circle sector type 428A. The fifth circle sector type 428A may have an arc length corresponding to (or near to) 180°. In some cases, the hub electrodes 235A of the third, fourth, and fifth sector type may be inserted and connected in a similar manner as discussed in FIG. 4C.

In this manner, the hub electrodes 235A may be arranged in different arrangements that have trade-offs. For instance, uniform arc length circle sectors may ensure each electrode is in contact with a similar amount of skin to sense biopotential signals, while non-uniform arc length circle sectors may provide a greater range of functionality (e.g., for sensing ECG data, or sensing different combinations of bio-electrical activity). Moreover, in the cases where switches or a multiplexer enable dynamic signal paths (e.g., to different differential amplifiers 315 or the ECG chip 270), different combinations (based on configuration data for each connections state) of the circle sector electrodes may be used for biopotential sensing or as reference electrodes.

In some cases, the hub electrodes 235A may include electrodes of different form factors (e.g., the first circle sector type 414, the second circle sector type 416, and the like, as discussed herein). The electrodes of different form factors may include sets of at least two electrodes of a same form factor or sets of at least two electrodes that have different form factors and same surface areas. In this manner, electrodes that have a same form factor or a same surface area may be input connection points 310B of a same differential amplifier 315. For instance, a pair of electrodes of the first circle sector type 414, or a pair of electrodes of the second circle sector type 416, may have a same surface area (and form factor). The pair of electrodes may input biopotential signals to connection points 310B of a same differential amplifier 315. In some cases, the differential amplifier 315 may subtract the biopotential signals correctly if the signals are from electrodes of equal surface area. Thus, in some cases, all electrodes in an array may have equal surface area or not, but each pair of electrodes which forms a channel may have equal surface areas.

In some cases, the surface area of the hub electrodes 235A may be larger or smaller for different form factors. Larger surface area form factors may have a greater resistance to noise (as compared to smaller surface area form factors). In this case, larger surface area form factors may provide for a more resilient system over all. Smaller surface area form factors may provide space for additional electrodes and channels (as compared to larger surface are form factors). In this case, having more electrodes and channels may provide additional biopotential signals to provide greater classification breadth (e.g., enable classifying a larger number of a plurality of gestures as compared to larger surface area form factors). In some cases, providing more channels may be useful for more complicated inferences in machine learning model. For example, a machine learning model may classify a smaller number of gestures using fewer channels, while the machine learning model may classify a larger number of gestures using a greater number of channels.

In some cases, size of the hub electrodes 235A may also enable placement of electrodes where better (or different) placements may enable better signal quality (or signals for different gestures). For instance, certain locations on a wrist or forearm may provide better signals (for certain gestures) and electrodes may take certain shapes or surface areas to accommodate the locations where the better signal is located.

In some cases, symmetry of (at least a some) of the hub electrodes 235A along an axis (such as the at least one axis 415) may match (or align with) areas of symmetry in the wrist or forearm. For instance, a symmetrical layout may enable left and right wrist use, as the muscles in wrists are functionally symmetrical.

Thus, various arrangements and selections of form factor may be designed. Each such arrangement and selection may have different benefits and tradeoffs.

FIGS. 5A-5E depict graphics 500A, 500B, 500C, 500D, and 500E of different aspects of a biopotential sensor 205 of a wearable device 110 with hub electrodes 235A and wristband electrodes 235B. The different aspects of the biopotential sensor 205 of the wearable device 110 in graphics 500A, 500B, 500C, 500D, and 500E may apply to the wearable device 110, as discussed in FIGS. 1, 2A-2C, 3A-3C, and 4A-4D above. Graphics 500A, 500B, 500C, 500D, and 500E may be modified to have different arrangements and include less or more components as shown.

Figure 5A:
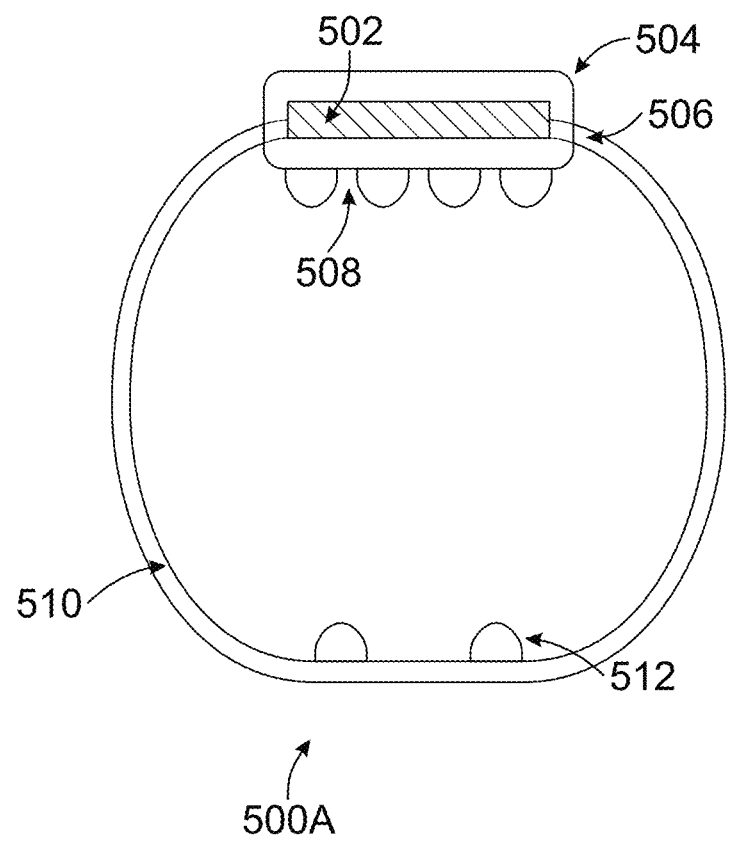
FIGS. 5A-5E depict graphics of different aspects of a biopotential sensor of a wearable device with hub electrodes and wristband electrodes.

In FIG. 5A, graphic 500A may depict a wearable device 110 with hub electrodes 508 (corresponding to hub electrodes 235A) and wristband electrodes 512 (corresponding to wristband electrodes 235B). The wearable device 110 may include a hub 504 with a biopotential chip 502 (corresponding to biopotential chip 250) disposed inside the hub 504. The hub 504 may have a sealed housing. The sealed housing may be water and/or air impermeable.

In some cases, the hub 504 may be rigid (e.g., made out of plastic or metal, and the like). In some cases, the hub 504 may be flexible (e.g., made out of silicon or a rubber, and the like). In some cases, the hub 504 may be 504 may include multiple rigid segments to enable a "semi flexible" behavior. For instance, the hub 504 may have rigid segments with joints that bend to allow for a degree of flexibility (see, e.g., wristband 510 in graphic 600B-2 as an example of this type of structure). The hub 504 may have the hub electrodes 508 (e.g., a plurality of hub electrodes 508) disposed on an interior surface of the hub 504, so as to contact a user's arm (e.g., wrist or forearm). For instance, the hub 504 may be positioned over the top of a user's wrist, so that the hub electrodes 508 may sense biopotentials from the top of the wrist.

The biopotential chip 502 may include the plurality of analog inputs 305 and the plurality of ADCs 250E configured to receive signals from the plurality of analog inputs 305, as discussed herein. The biopotential chip 502 may also receive signals from the accelerometer and the gyroscope, as discussed herein. The hub electrodes 508 may be electrically connected, via conductors disposed within the hub 504, to one or more analog inputs 305 of the plurality of analog inputs 305 of the biopotential chip 502.

Figure 5B:
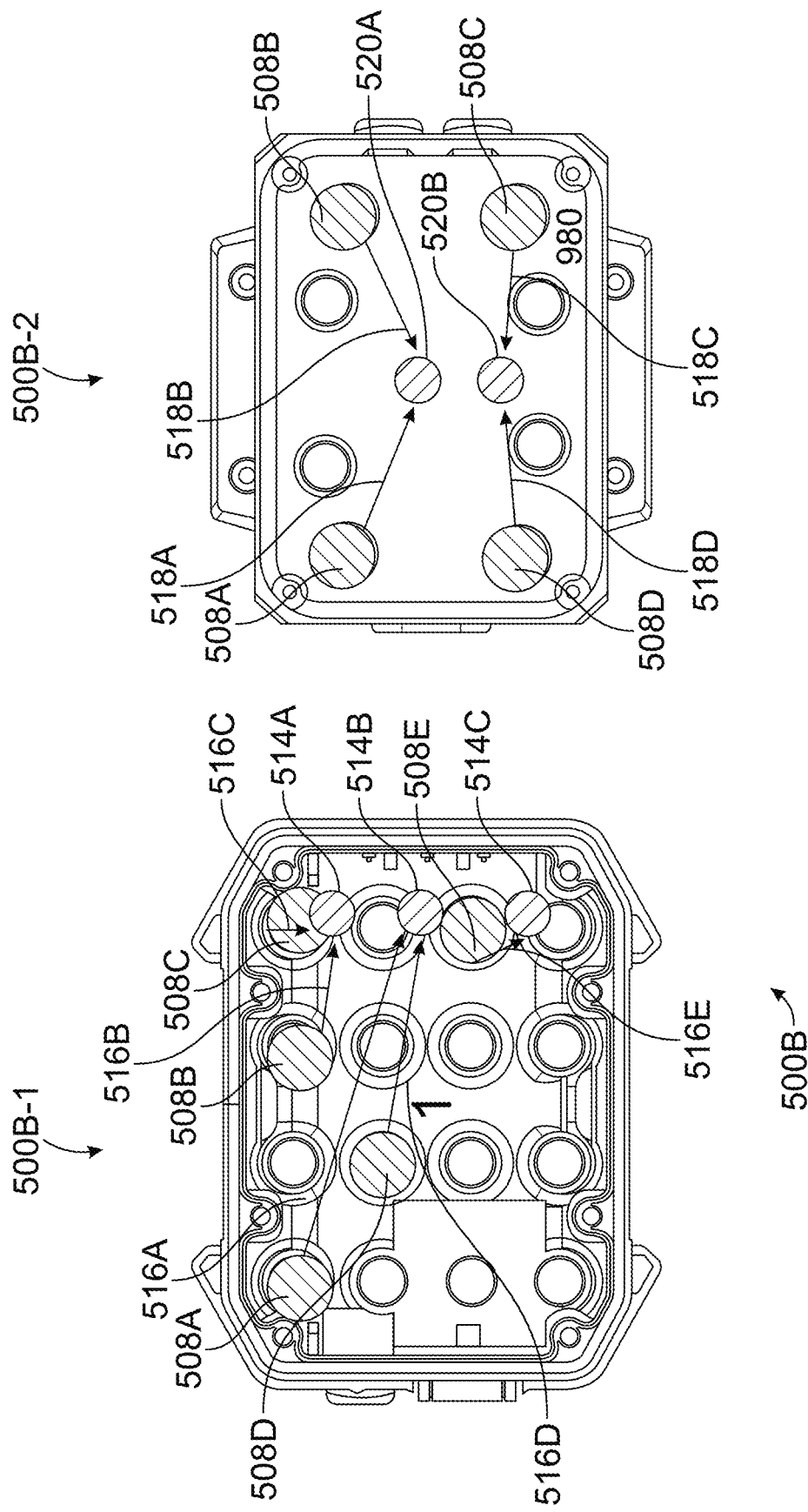
Figure 5C:
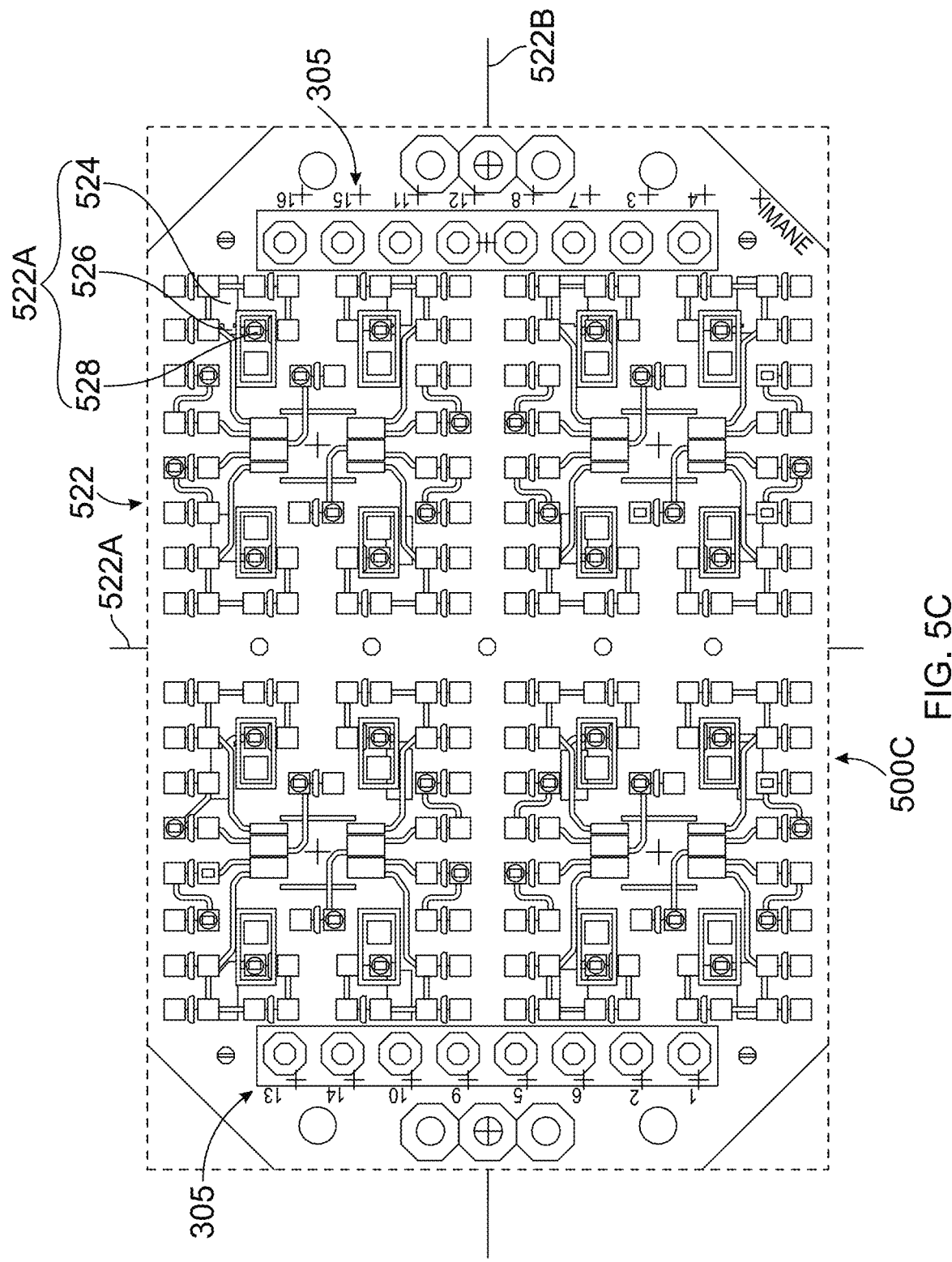
Figure 5D:
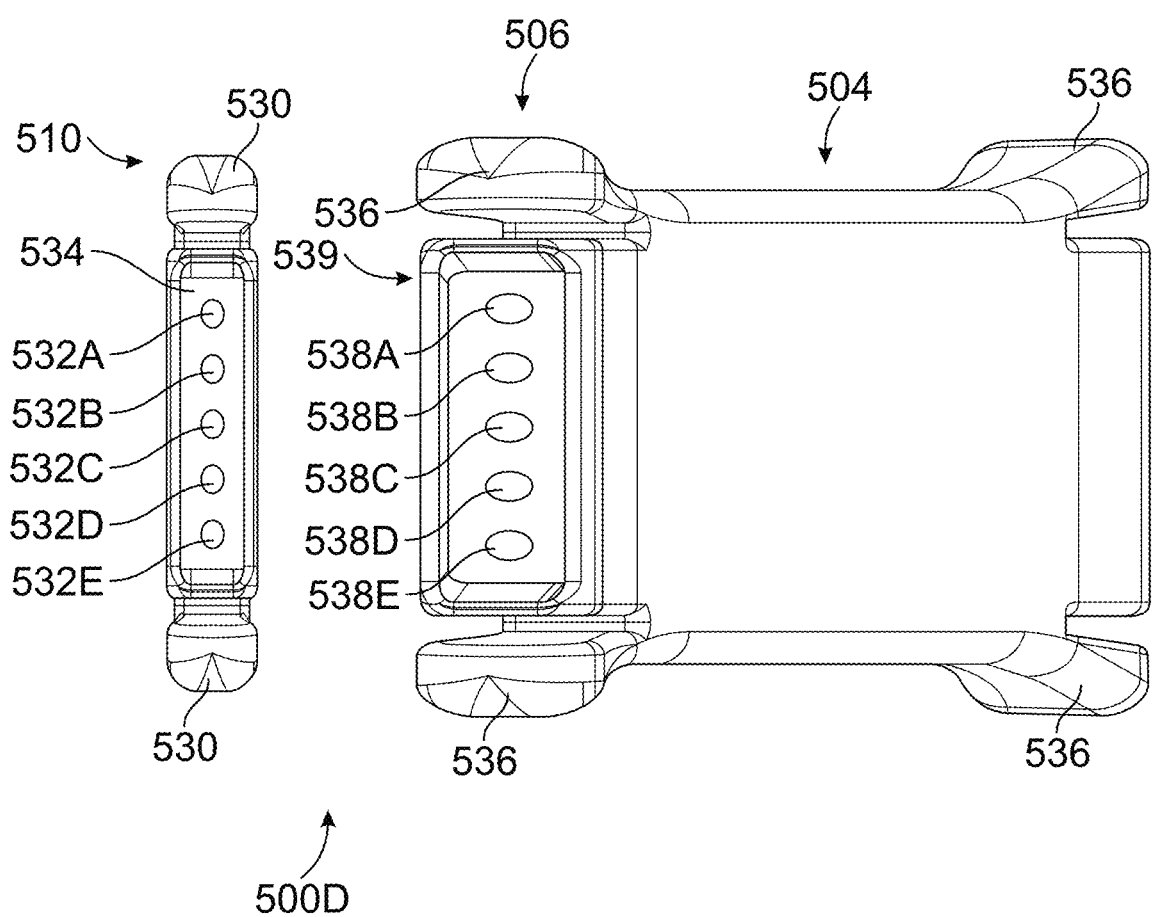
Figure 5E:
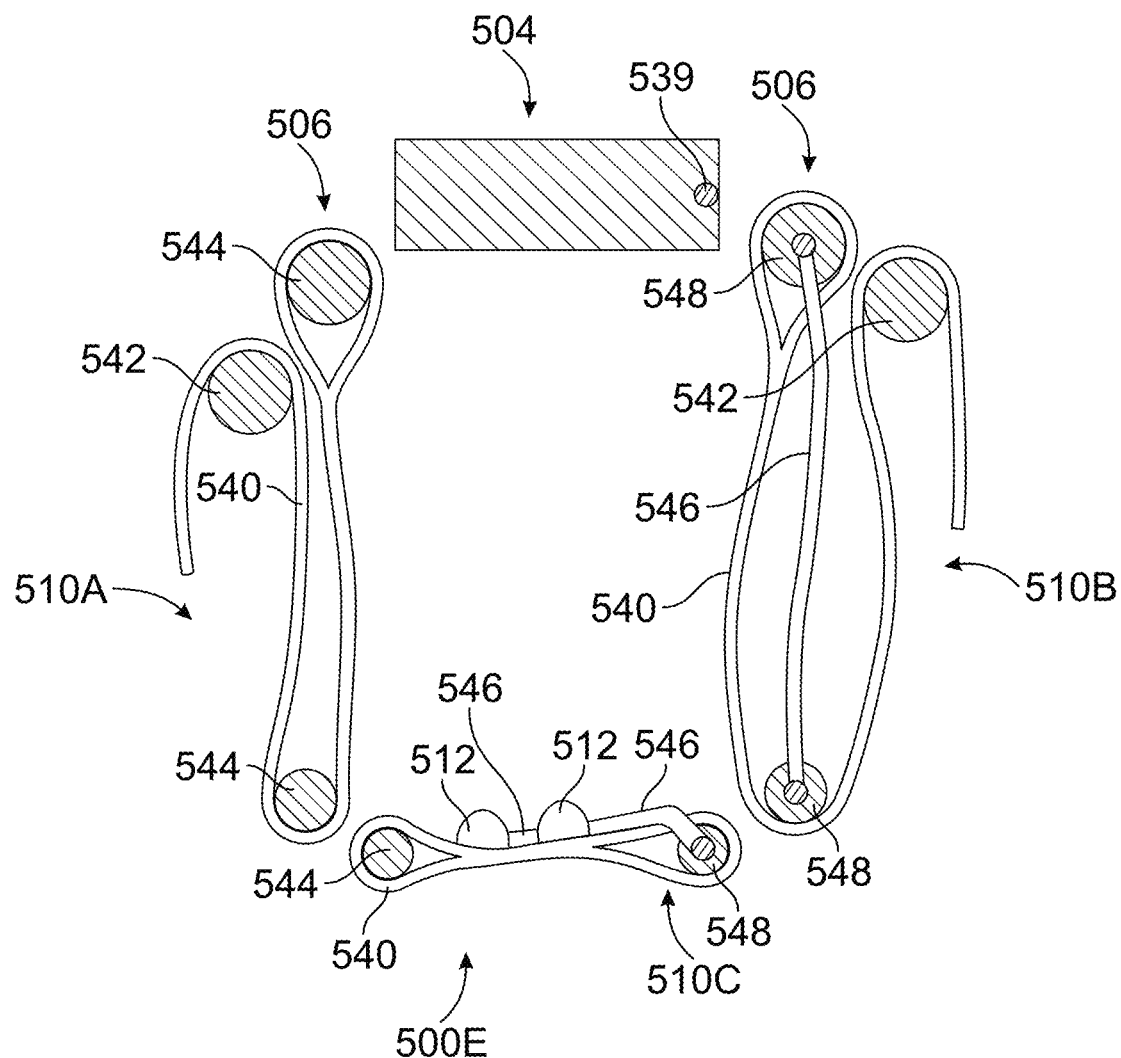

The sealed housing of the hub 504 may include an electrical port 539 (see FIG. 5D or 5E). The electrical port 539 may be electrically connected to at least one analog input (e.g., on a one-to-one basis for a number of wristband electrodes 512) of the plurality of analog inputs 305 of the biopotential chip 502. In some cases, the electrical port 539 may also include a connection to a voltage source of the biopotential chip 502, so as to provide power to the wristband electrodes 512.

The wearable device 110 may include a wristband 510. The wristband 510 may be made out suitable materials, such as textiles, metal, silicon, rubber, plastic, and the like. The wristband 510 may have the wristband electrodes 512 (e.g., one or more, or a plurality of wristband electrodes 512) disposed on an interior surface of the wristband 510, so as to contact a user's arm (e.g., wrist or forearm). For instance, the wristband 510 may be configured so that the wristband electrodes 512 are generally placed in a same location on a user each time the wearable device 110 is worn by the user.

In some cases, the wristband 510 is a closed loop (e.g., does not open). In these cases, the wristband 510 may be adjustable or stretchy to fit over a hand of a user. In some cases, the wristband 510 is configured to be opened and closed by a clasp, or other suitable locking mechanism. In some cases, a wristband electrode 512 may be a part of the clasp or other suitable locking mechanism. The wristband 510 may have one or more wristband conductors to carry biopotential signals from the wristband electrodes 512 to the biopotential chip 502, as discussed herein. For instance, the one or more wristband conductors may electrically connect the wristband electrodes 512 to the electrical port 539 of sealed housing of the hub 504. The wristband 510 and the hub 504 together may be configured to encircle the wrist (or forearm) of the user 105. In some cases, the one or more wristband conductors may be a conductive fabric. In some cases, the one or more wristband conductors may be signal conductors (e.g., wires) that are shielded (or not). For instance, the signal conductors may be embedded into the wristband 510 or attached to an exterior (or interior) surface of the wristband 510.

The wearable device 110 may also have a hub-wristband junction 506. The hub-wristband junction 506 may secure the wristband 510 to the hub 504. For instance, the hub-wristband junction 506 may secure the wristband 510 to the hub 504 on two sides of the hub 504. The hub-wristband junction 506 may be in a same location as the electrical port 539 of the sealed housing of the hub 504, so that the one or more wristband conductors may pass electrically signals into the hub 504 via the electrical port 539.

In this manner, the wearable device 110 may obtain biopotential data based on signals received by both hub electrodes 508 and wristband electrodes 512 and processed by the ADCs 250E of the biopotential chip 502. In some cases, the biopotential chip 502 may obtain wrist location data based on outputs from the accelerometer and the gyroscope, and the biopotential chip 502 may be configured to transmit the biopotential data and the wrist location data to a ML classifier 230, discussed herein. The ML classifier 230 be configured to analyze the biopotential data and the wrist location data to generate a gesture output indicating a gesture performed by the user 105.

In some cases, the hub electrodes 508 are disposed in a curved arrangement. The curved arrangement may have a curvature in a plane that extends perpendicular to a length of the forearm when the wearable device 110 is worn on the wrist. For instance, the curvature may correspond to a curved surface with a radius equal to a shallowest curvature of a distribution of user wrists (or forearms). The distribution may be a distribution of an expected population of users (e.g., military users would have a larger wrist or forearm, while civilian population may have smaller wrists or forearms). The shallowest curvature may be within a selected standard deviation of a mean curvature to avoid capturing outliers in a distribution. In other cases, a radius of curvature may be less than 0.5 cm, less than 1 cm, less than 2 cm, less than 3 cm, less than 4 cm, or less than 5 cm. In this manner, hub electrodes 508 may have a consistent fit that may apply across a population of users.

In some cases, the wristband electrodes 512 may be active electrodes. In this case, the wristband electrodes 512 may be coupled to buffer components (such as one or more wristband amplifiers). The buffer components (e.g., the one or more wristband amplifiers) may be disposed between the wristband electrodes 512 and the one or more wristband conductors. The buffer components may be configured to amplify signals received by the wristband electrodes 512 to buffer the signals from noise and/or interference as the signals travel through the one or more wristband conductors.

In some cases, the wristband 510 may be adjustable to a plurality of length states. In this case, each of the plurality of length states may have a respective circumference when the wristband 510 is worn. Moreover, the wristband 510 and the wristband electrodes 512 may be configured so that the wristband electrodes 512 may be situated at a constant position relative to the hub 504 in each of the plurality of length states. In this manner, the wristband electrodes 512 may be disposed at a predetermined position on the user's wrist (or forearm) across a range of wrist sizes of users.

In some cases, the wristband 510 may connect to the hub 504 on two sides of the hub 504, at the hub-wristband junction 506. In some cases, the wristband 510 may be adjustable relative to the hub 504 on both of the two connections between the wristband 510 and the hub 504. In some cases, the wristband 510 may be adjustable on only one of the two connections between the wristband 510 and the hub 504. In some cases, the wristband 510 may not be adjustable on the two connections between the wristband 510 and the hub 504. Thus, in cases where the wristband 510 is adjustable, the adjustment may enable precise (and consistent) placement of electrodes relative to the location of electrode signals, even across various wrist shapes and sizes. In some cases, the adjustment on both sides may be made while still allowing electrical connection between wristband electrodes in the wristband 510 and the hub 504, or across various electrodes in the wristband 510.

In some cases where both sides are adjustable, a first side of the wristband 510 may lock more securely than a second side of the wristband 510. For, the first side may be adjusted to secure the wristband electrodes to the position for a user's wrist once, and the user may use the second side to put the device on and take the device off. In some cases, the first side may where the electrical port 539 is located.

In FIG. 5B, graphic 500B shows aspects of trace lengths of conductors connecting the hub electrodes 508 to the analog inputs 305. For instance, in graphic 500B-1, the hub electrodes 508A, 508B, 508C, 508D, and 508E may have respective trace lengths 516A, 516B, 516C, 516D, and 516E to locations 514A, 514B, and 514C of certain analog inputs 305. The trace lengths 516A, 516B, 516C, 516D, and 516E may be significantly different (e.g., a longest trace length being more than double or triple in length as compared to a smallest trace length). Thus, biopotential signals being carried on the trace lengths 516A, 516B, 516C, 516D, and 516E may be exposed to environmental electrical noise to differing degrees, in accordance with their trace length. Thus, the biopotential signals may have differing signal to noise ratios that may be a challenge to filter out (e.g., via differential amplifiers 315).

In contrast, in graphic 500B-2, the hub electrodes 508A, 508B, 508C, and 508D may have respective trace lengths 518A, 518B, 518C, and 518D to locations 520A and 520B of certain analog inputs 305. The trace lengths 518A, 518B, 518C, and 518D may be significantly similar (e.g., within 5%, 3%, or 1% of each other). Thus, biopotential signals being carried on the trace lengths 518A, 518B, 518C, and 518D may be exposed to environmental electrical noise to a similar degree, in accordance with their trace length. By using equal trace lengths, common noise (such as 60 Hz radiofrequency noise) may apply equally to the various traces, and this noise may be effectively cancelled using differential amplifiers or other signal averaging circuitry or logic. Thus, the biopotential signals may have similar signal to noise ratios that may be a relatively easier to filter out (e.g., via differential amplifiers 315). For instance, the locations 520A and 520B of certain analog inputs 305 may be relatively equidistant to each of the hub electrodes 508A, 508B, 508C, and 508D. In contrast, the locations 514A, 514B, and 514C of certain analog inputs 305 may be relatively closer to certain of the hub electrodes 508A, 508B, 508C, 508D, and 508E and relatively further from others of hub electrodes 508A, 508B, 508C, 508D, and 508E.

In FIG. 5C, graphic 500C depicts trace lengths of conductors 522 from hub electrodes 508 to analog inputs 305 in a different arrangement. The arrangement of conductors 522 may have at least two axis of symmetry, such a first axis of symmetry 522A and a second axis of symmetry 522B. Due to the first axis of symmetry 522A and the second axis of symmetry 522B, the trace lengths may significantly similar. In particular, the conductors 522 may be sixteen (16) identical circuits, each positioned proximate (e.g., within a threshold distance) to a respective electrode. As each conductor 522, has an identical circuit protecting the biopotential signal from each individual electrode, the sixteen biopotential signals are exposed to the same amount of noise (e.g., a variation less than 1%).

In some cases, each conductor 522A (of conductors 522) may have a spring contact 524, a trace 526, and a buffer circuit 528. The spring contact 524 may electrically connect directly to an electrode (e.g., below the spring contact 524, that is into the graphic 500C). The spring contract 524 may be a biased deformable conductive metal to ensure electrical connection to the electrode even in the presence of vibration or shock. The trace 526 may be an electrical conduit on a PCB board. The trace 526 may be a very short trace (e.g., less than 1 mm, less than 2 mm, less than 3 mm, less then 4 mm, and the like) electrically connecting the spring contact 524 and the buffer circuit 528. In some cases, the trace 526 may be configured to a top layer of a PCB and connected to the buffer circuit 528. Thus, in this manner, the electrodes may be as close as possible to the buffer circuit, and thus reduce exposure of the biopotential signals to noise. The buffer circuit 528 may include buffer components and electrically connect the electrode (via the spring contact 524 and the trace 526) to an analog input 305. The buffer circuit 528 may protect the biopotential signals from noise by various means, as discussed herein. In FIG. 5D, graphic 500D may depict the hub-wristband junction 506 of the hub 504 to secure the wristband 510 to the hub 504 and pass signals (and power) between the wristband 510 and hub 504 with a non-adjustable connection (to adjust a length of the wristband 510). For instance, each of a first end and second end of the wristband 510 may have first connectors 530 configured to connect to second connectors 536 of the hub-wristband junction 506. In some cases, the first connectors 530 and second connectors 536 may be a snap fit, a ball-joint connection, and the like. For instance, the second connectors 536 may flex while the first connectors 530 are inserted, and flex back to hold the first connectors 530 after the first connectors 530 are fully inserted.

Also depicted in graphic 500D, wristband conductors 532A, 532B, 532C, 532D, and 532E may be embedded in a material 534 (e.g., textile, rubber, silicon, and the like) of the wristband 510. After the first connectors 530 are connected to the second connectors 536, the wristband conductors 532A, 532B, 532C, 532D, and 532E may be electrically connected (e.g., by insertion and/or contact, and the like) to corresponding electrical junctions 538A, 538B, 538C, 538D, and 538E of the electrical port 539 of the sealed housing of the hub 504. For instance, one of electrical junctions 538A, 538B, 538C, 538D, and 538E may provide power to wristband electrodes 512, while four of electrical junctions 538A, 538B, 538C, 538D, and 538E may receive signals from the wristband electrodes (e.g., in the case of four wristband electrodes 512).

Accordingly, as shown the exemplary embodiment of FIG. 5D, a wristband may have biopotential electrodes, and wire traces carrying signals from those wristband electrodes may connect to a hub of a smartwatch using an electrical port on the hub. In some embodiments, the band may mechanically and releasably couple (e.g., via snap fit or latch) to the hub, and in the process of being mechanically coupled, and electrical connection between the wristband electrodes and processing circuitry (such as that described above with reference to FIGS. 2-3) may automatically be established, without need for separate mechanical and electrical connections. This may advantageously allow for simple and intuitive connections between wristband and hub, so that wristbands may easily be released and replaced, e.g., for user customization in sizing or style, or to replace damaged items.

In FIG. 5E, graphic 500E may depict the hub-wristband junction 506 of the hub 504 to secure the wristband 510 to the hub 504 and pass signals (and power) between the wristband 510 and hub 504 with an adjustable connection on both sides (to adjust a length of the wristband 510). At each hub-wristband junction 506, the wearable device 110 may have one of a first retention member 544 or a second retention member 548. For instance, the first retention member 544 may be textile retainer (e.g., a bar) that may be configured to open and close to retain a first portion of the wristband 510A (e.g., made of textile 540). The second retention member 548 may be textile retainer (e.g., a bar) that may be configured to open and close to retain a second portion of the wristband 510B (e.g., made of textile 540). The second retention member 548 may also pass electrical signals to electrical junctions 538A, 538B, 538C, 538D, and 538E of the electrical port 539 (preferably, a combined electrical port/mechanical coupling) of the sealed housing of the hub 504. For instance, the second retention member 548 may pass the electrical signals via an electrical conductor (e.g., a wire or slip ring).

The first portion of the wristband 510A and the second portion of the wristband 510B may be connected by a third portion of the wristband 510C, via additional first retention members 544 and second retention members 548. The third portion of the wristband may include the wristband electrodes 512 and be made of textile 540. Thus, the power and signals may be transmitted between the wristband electrodes 512 and electrical port 539 via wristband conductors 546.

The first retention member 544 and the second retention member 548 may each be paired with an adjustment member 542. The adjustment member 542 may lock the textile 540 of each of the first portion of the wristband 510A and the second portion of the wristband 510B in place (e.g., by compression, tension, or torsion).

It is desirable that electrodes 512 be able to maintain a common radial location on the lower side of a user's wrist regardless of the size of the user's wrist. The ML classifier may be trained based on an expectation that the electrodes will be located in or near that predetermined radial location, which has known electrical relationships to the muscles and nerves of the arm and wrist. In conventional wristbands that are tightened on only one side, tightening the band moves the material of the band relative to the wrist, which, if electrodes were incorporated, would result in the electrodes being undesirably shifted relative to the wrist. Conversely, in the embodiment shown in FIG. 5E (and in other embodiments within the scope of this disclosure), the size of the wristband may be adjusted while the position of the wristband electrodes relative to the wrist is maintained.

FIGS. 6A-6D depict graphics 600A, 600B, 600C, and 600D of different aspects of wristband electrodes 512 (corresponding to wristband electrodes 235B) of a biopotential sensor 205. The different aspects of the wristband electrodes 512 of the biopotential sensor 205 in graphics 600A, 600B, 600C, and 600D may apply to the wearable device 110, as discussed in FIGS. 1, 2A-2C, 3A-3C, 4A-4D, and 5A-5E above. Graphics 600A, 600B, 600C, and 600D may be modified to have different arrangements and include less or more components as shown.

Figure 6A:
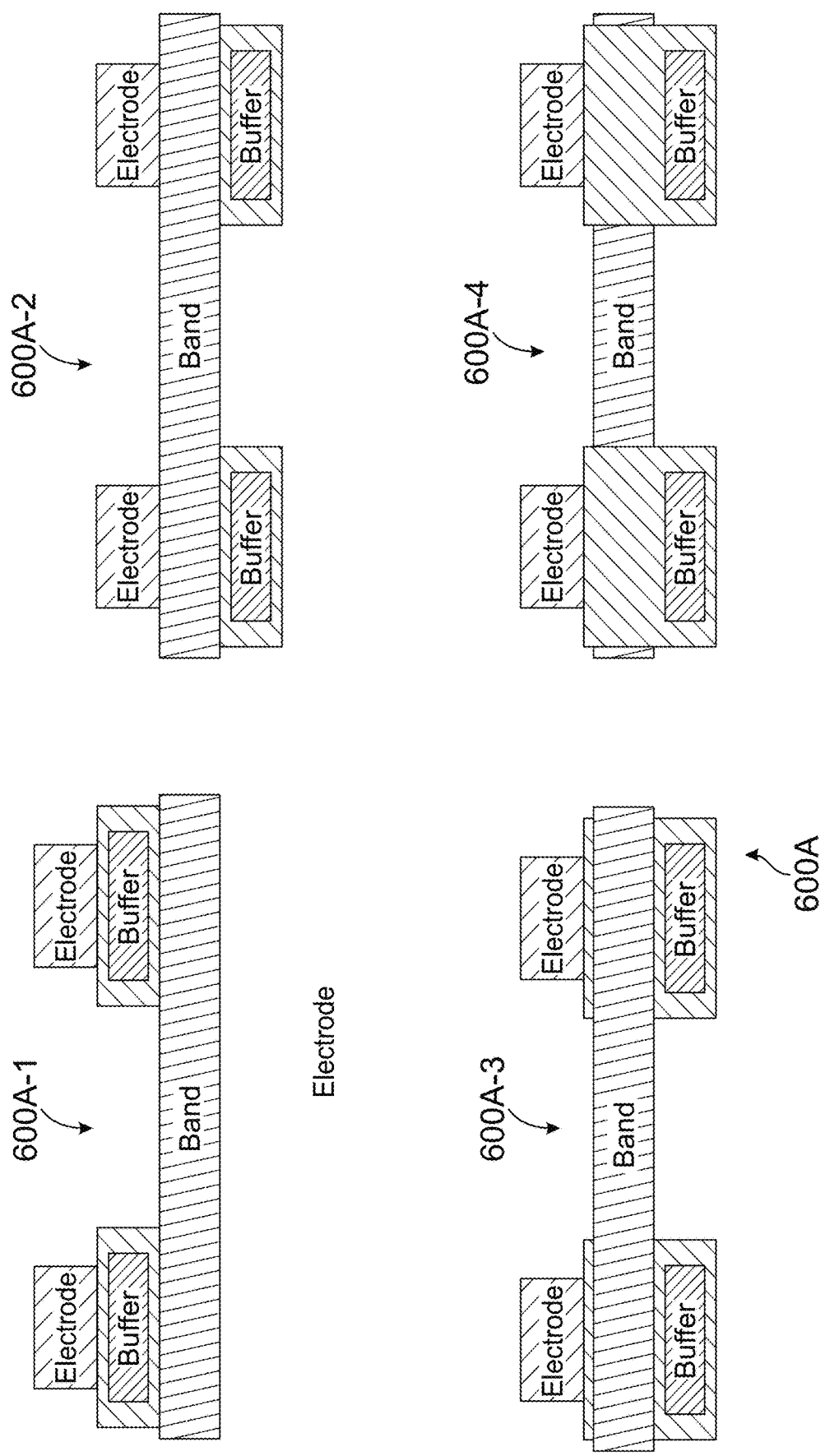

In FIG. 6A, graphic 600A may depict different arrangements of buffer components and housings of active wristband electrode 512. In graphic 600A-1, the housing is attached to an interior of the wristband with the buffer components sealed inside and an electrode attached to the housing on an interior of the wristband. In graphic 600A-2, the housing is attached to an exterior of the wristband with the buffer components sealed inside and an electrode attached to an interior of the wristband and connected to the buffer components via, e.g., a wristband conductor or the electrode extends through the wristband. In graphic 600A-3, the housing is attached to an exterior of the wristband with the buffer components sealed inside and an electrode attached to the housing on the interior of the wristband, as the housing may extend through a portion of the wristband. In graphic 600A-4, the housing is attached to and surrounds the wristband with the buffer components sealed inside and an electrode attached to an interior facing side of the housing on an interior of the wristband.

Figure 6B:
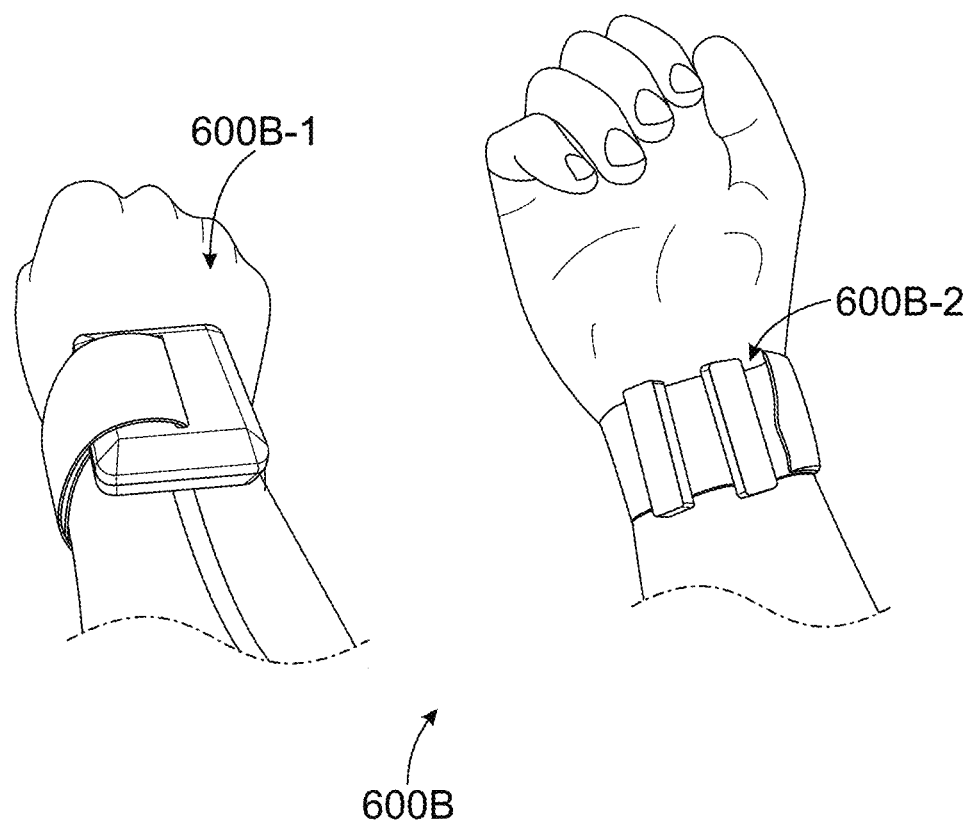

In FIG. 6B, graphic 600B may depict an active electrode housing for wristband electrodes 512 surrounding the wristband 510 (in graphic 600B-2) and a hub 504 (in graphic 600B-1).

In FIG. 6C, graphic 600C may depict textile wristband electrodes 512 (in graphic 600C-1) and conductors from the electrical port 539 connecting to analog inputs 305 (in graphic 600C-2).

Figure 6D:
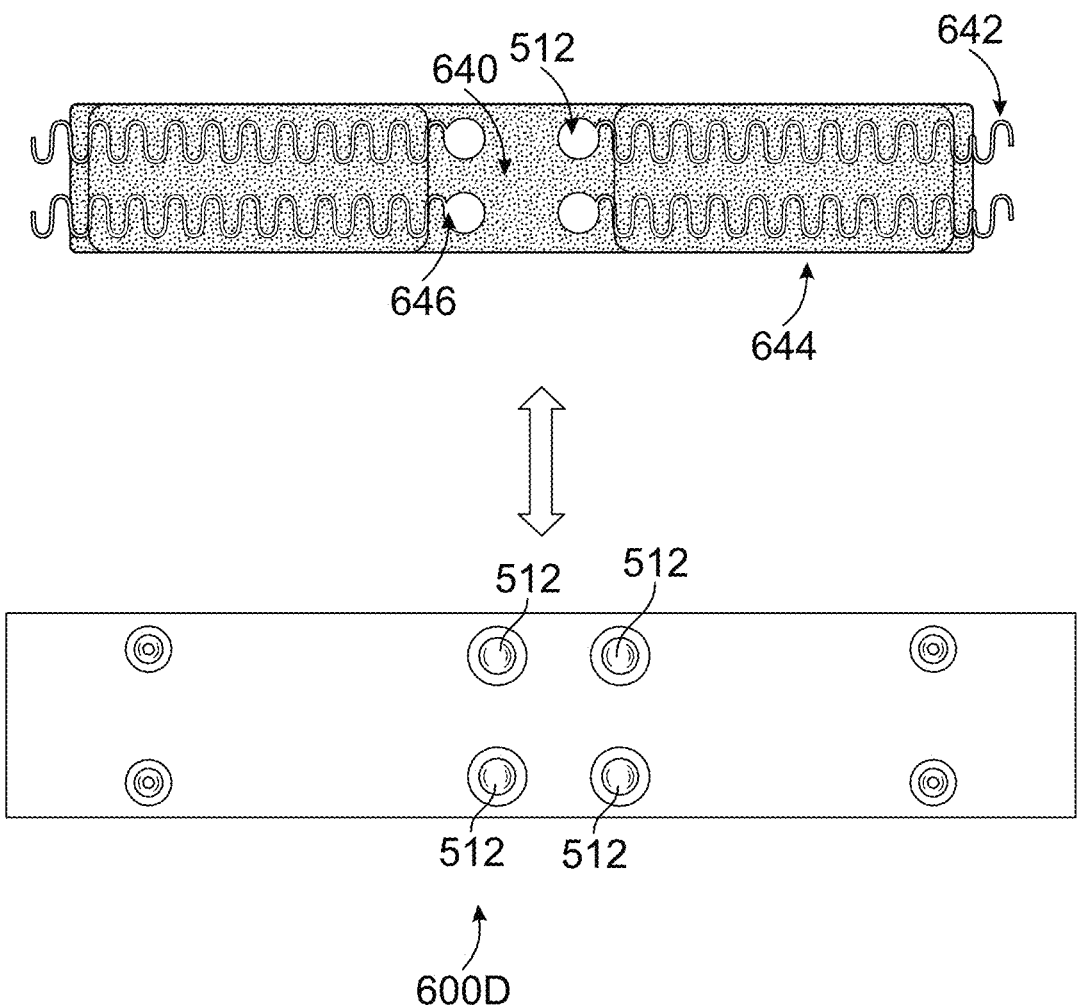

In FIG. 6D, graphic 600D may depict features of textile wristband electrodes 512. For instance, the wristband 510 may include portions e-textile that includes wristband conductors 646 shielded using a shield 644 (e.g., a layer of textile or laminate covering the wristband conductors on a textile). The textile wristband electrodes 512 may be e-textile fabric thread (metal filament and the like) that is built into a shape to act as an electrode. The textile wristband electrodes 512 may be connected to the wristband conductors 646, which may run the electrical port 539 where extensions 642 of wristband conductors 646 may be connected to the electrical port 539. In this case, the textile wristband electrodes 512 may "passive electrodes" that do not have buffer components. Moreover, in this case, the wristband 510 may include a middle region of textile 640 between the textile wristband electrodes 512 to provide stretch to the wristband 510. Furthermore, the wristband conductors 646 may be shaped in certain arrangements (e.g., sine wave) to elongate with a stretching of the e-textile.

Figure 7B:
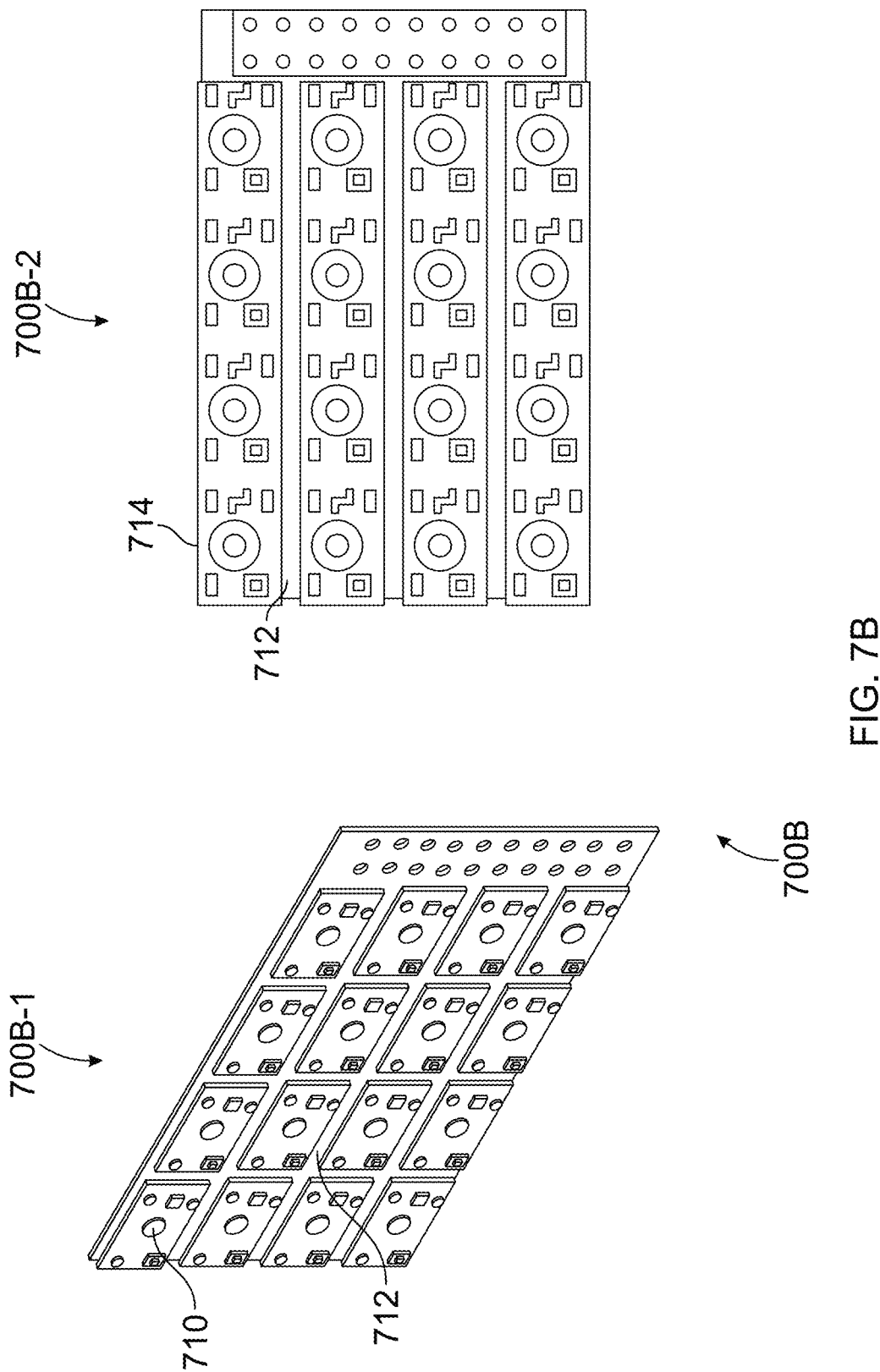

FIGS. 7A-7B depict graphics 700A and 700B of different aspects of hub electrodes 235A disposed in a curved arrangement. The different aspects of the hub electrodes 235A disposed in a curved arrangement in graphics 700A and 700B may apply to the wearable device 110, as discussed in FIGS. 1, 2A-2C, 3A-3C, 4A-4D, 5A-5E, and 6A-6D above. Graphics 700A and 700B may be modified to have different arrangements and include less or more components as shown.

In FIG. 7A, graphic 700A may depict different perspectives of a curved arrangement of hub electrodes 508. In graphic 700A-2, the hub electrodes 508 are depicted arranged in an array (e.g., four by four matrix). The curved arrangement of the array may have a curvature in a plane 702 that extends perpendicular to an axis the length of the forearm when the wearable device 110 is worn on the wrist. The curved arrangement of the array may not have a curve in the axis the length of the forearm. In graphic 700A-1, the curvature in the plane 702 that extends perpendicular to the axis the length of the forearm may be recognized by the facing direction of hub electrodes 508. For instance, a plane 704 arranged normal from a face of hub electrode 508 from a first group (e.g., on far left) would intersect a plane 706 arranged normal from a face of hub electrode 508 from a second group (e.g., on far right).

In FIG. 7B, graphic 700B may depict how signals may be collected from the curved arrangement of hub electrodes 508. Generally, the hub electrodes 508 may be attached to a PCB 710 (graphic 700B-1) or PCB 714 (graphic 700B-2), with or without buffer components, to secure the hub electrodes 508 to the hub 504. In graphic 700B-1, each hub electrode 508 may have a single PCB 710 to attach to, and each PCB 710 may be independent of any other PCB 710 (that is not connected to other PCB 710 and may be flexible independent of the other PCB 710). Sets of hub electrodes 508 may be attached respective PCB 714, and each PCB 714 may be independent of any other PCB 714 (that is not connected to other PCB 714 and may be flexible independent of the other PCB 714). The sets of hub electrodes 508 may include hub electrodes along a row (or column) of the array, so that the PCB 714 may be curved into position in accordance with the curvature in the plane 702.

In both cases, the PCB 710 and PCB 714 are mounted to a flexible PCB 712. The flexible PCB 712 may carry signals to the biopotential chip 250 and power from the biopotential chip 250 to the hub electrodes 508.

In this manner, the hub electrodes 508 may be curved to match a curved surface of a user's wrist or forearm. Thus, the hub electrodes 508 may have more uniform contact between the electrode face and the user's skin, and generate more accurate biopotential data (and more accurate gesture detection).

In some cases, the hub 504 may also be flexible. The hub 504 and/or the PCBs may (combined) have a flex with spring constant to start in a flat arrangement and then the user 105 may strap the hub 504 down (and thereby curve the PCBs and electrodes 508) so that the hub electrodes 508 are in contact with skin of the user 105. In some cases, to strap down the hub, the straps may have attachment points at ends of the hub 504. In this case, this may be easier to attach straps to the hub 504. In some cases, the strap may strap down over top of the hub 504. In this case, it may be harder to attach the straps, but the force maybe evenly distributed across the hub electrodes 508. In this case, the curvature in the plane 702 (at default without straps) may correspond to a curved surface with a radius equal to median curvature of a distribution of user wrists (or forearms). The distribution may be a distribution of an expected population of users (e.g., military users would have a larger wrist or forearm, while civilian population may have smaller wrists or forearms). The median curvature may be selected from within one standard deviation of a mean curvature, preferably on the larger end of the distribution, so to flex down to the skin of users while being strapped down.

Figure 8A:
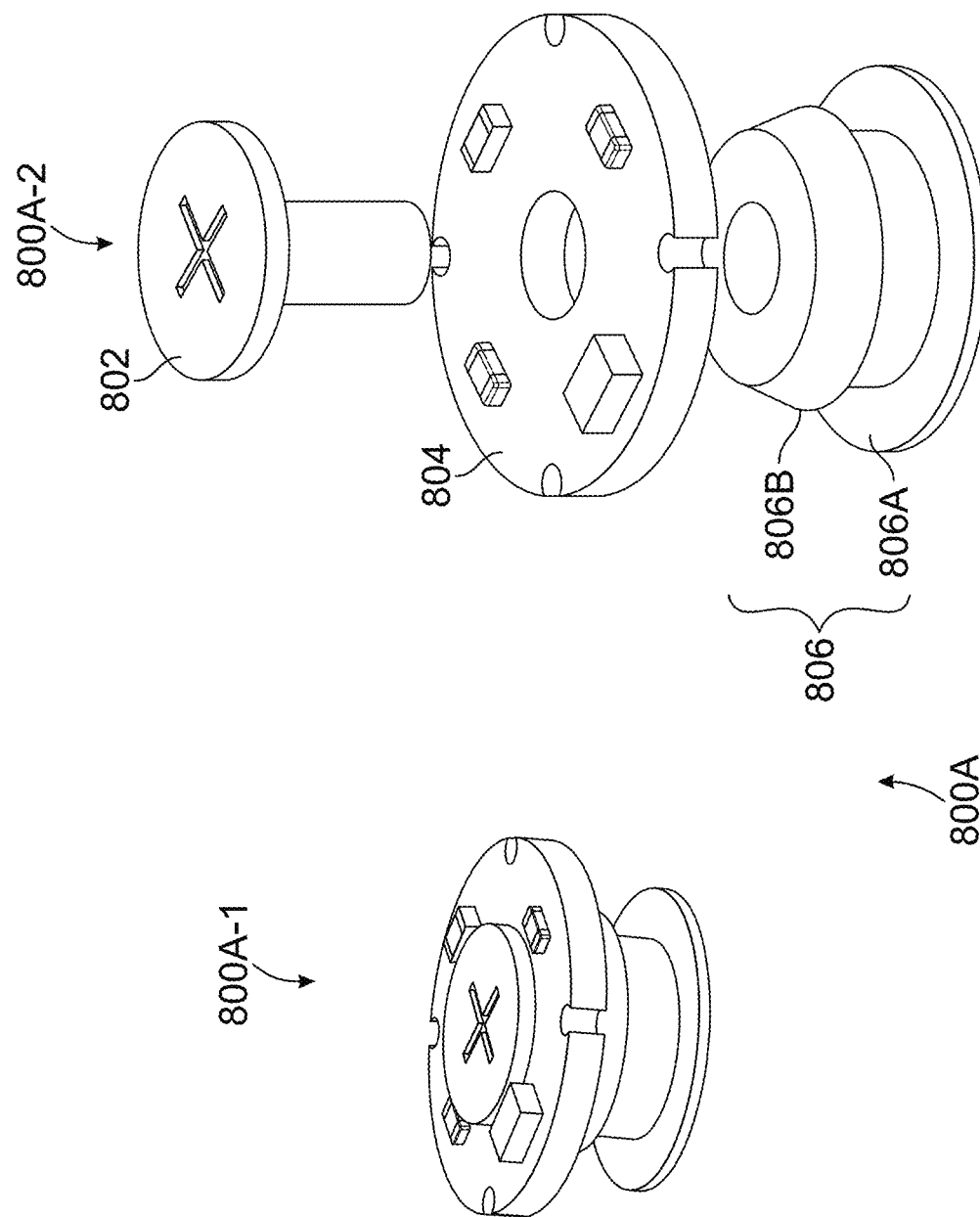
FIGS. 8A-8B depict graphics of different aspects of electrodes of a biopotential sensor.
Figure 8B:
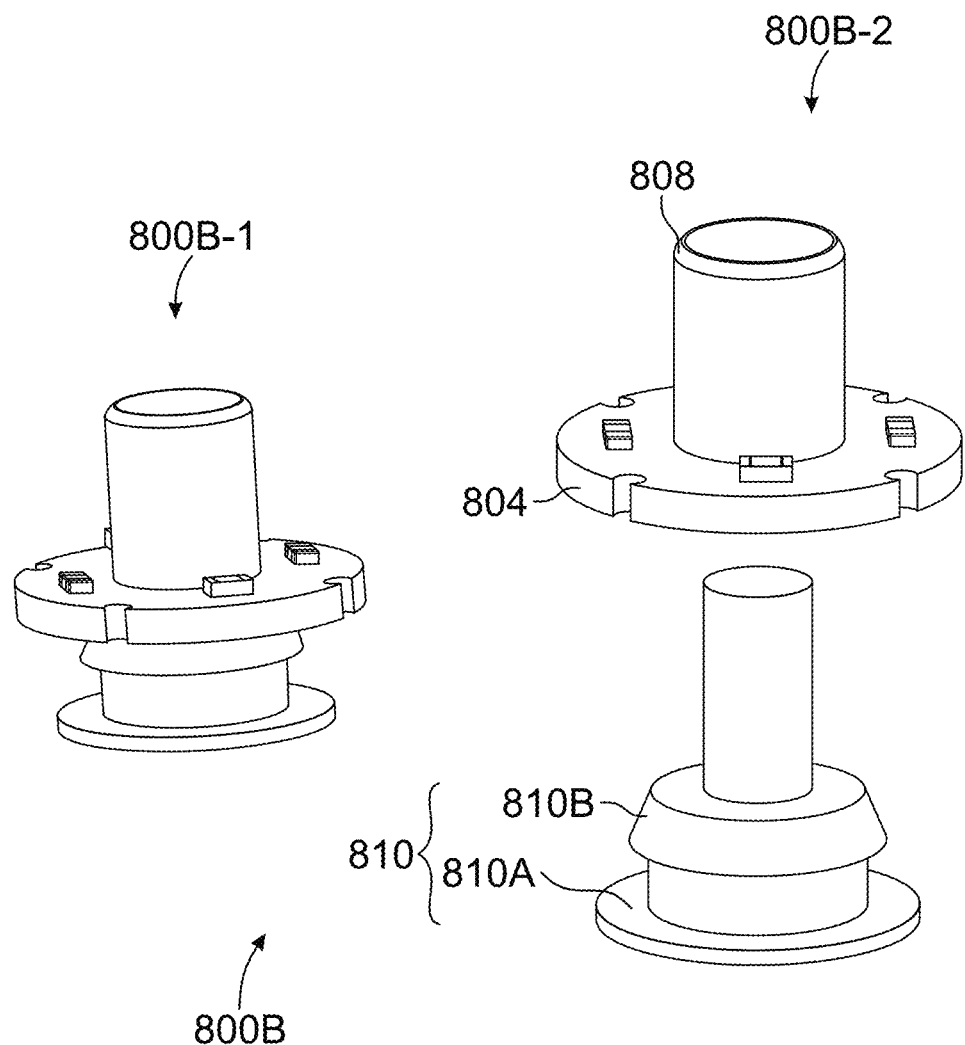

FIGS. 8A-8B depict graphics 800A and 800B of different aspects of electrodes 235 of a biopotential sensor 205. The different aspects of the electrodes 235 of the biopotential sensor 205 in graphics 800A and 800B may apply to the wearable device 110, as discussed in FIGS. 1, 2A-2C, 3A-3C, 4A-4D, 5A-5E, 6A-6D, and 7A-7B above. Graphics 800A and 800B may be modified to have different arrangements and include less or more components as shown.

In FIG. 8A, graphic 800A may depict an active electrode with a solid metal body 806 (as assembled in 800A-1, and in exploded form 800A-2) that affixes to a hub or case via a first retention member 802. The solid metal body 806 may include a face 806A and an extended portion 806B. The extended portion 806B may have a thread for engaging a corresponding thread of the first retention member 802. The first retention member 802 may affix the solid metal body 806 to the hub or case. In some cases, the PCB 804 (with buffer components) may be affixed by the first retention member 802 to the solid metal body 806 (and/or a portion of an interior of the hub or case).

In FIG. 8B, graphic 800B may depict an active electrode with a solid metal body 810 (as assembled in 800B-1, and in exploded form 800B-2) that affixes to a hub or case via a second retention member 808. The solid metal body 810 may include a face 810A and an extended portion 810B. The extended portion 810B may have a pressure fit portion (e.g., increasing in diameter away from the face) for engaging the second retention member 808. The second retention member 808 may be a hollow cylinder for receiving the extended portion 810B. The hollow cylinder may have tapering walls (e.g., decreasing in diameter toward the face). The second retention member 808 may affix the solid metal body 810 to the hub or case. In some cases, the PCB 804 (with buffer components) may be affixed to the second retention member 808 on an exterior of the hollow cylinder of the second retention member 808. In some cases, the active electrode may be attached to the housing of the hub 504 via a clip.

Example Routine(s)

Figure 9A:
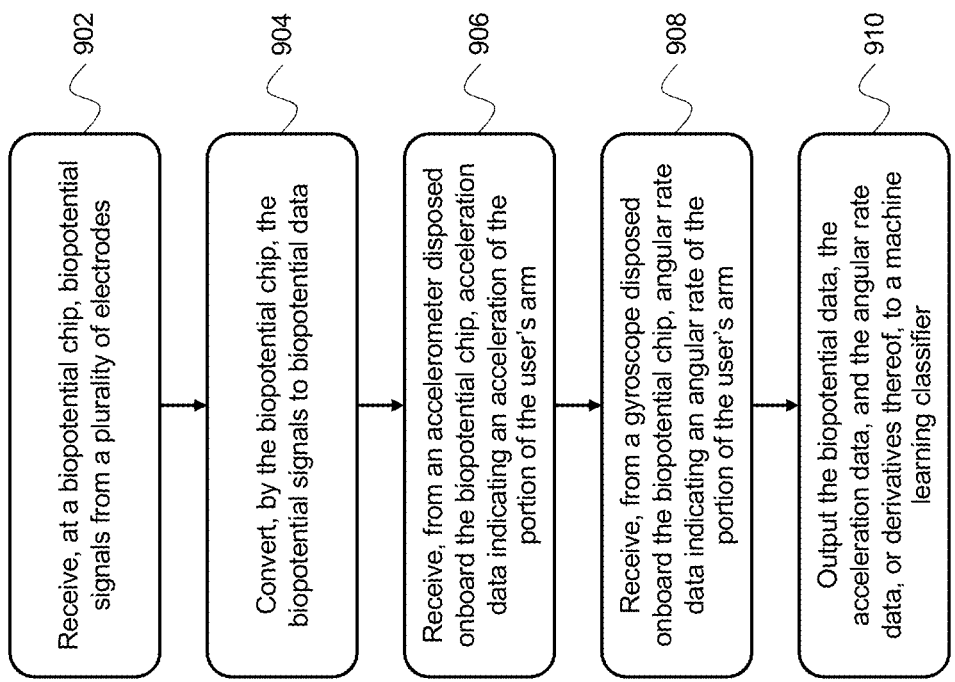
FIGS. 9A and 9B depict flowcharts of routines of a wearable device.
Figure 9B:
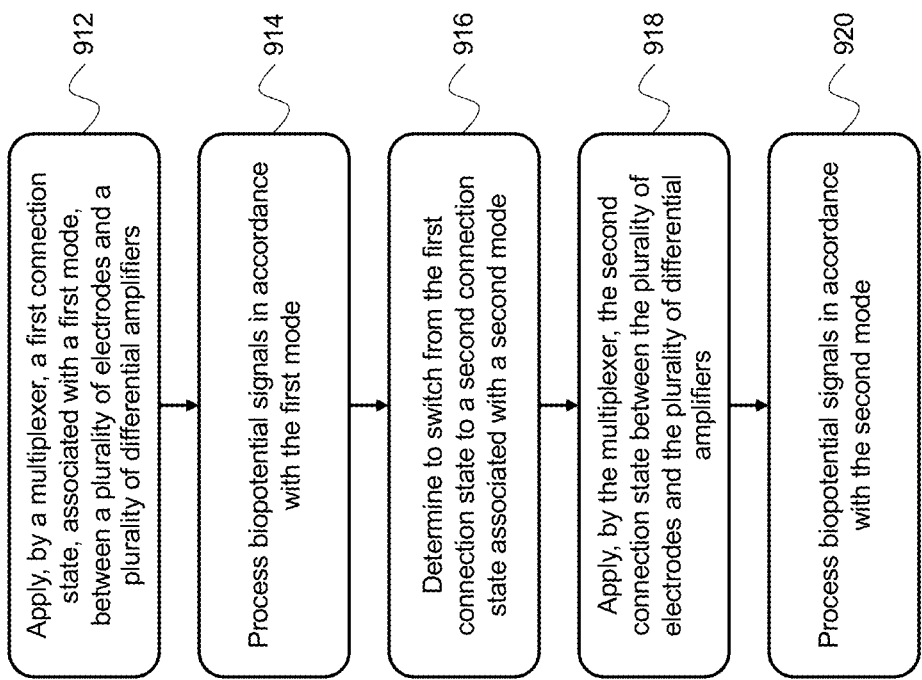

FIGS. 9A and 9B depict flowcharts of routines of a wearable device. FIG. 9A depicts a flowchart of an exemplary routine 900A for outputting gesture data to a ML classifier. In the routine 900A, the routine 900A may be performed by one or more systems, such as biopotential chip 250 that performs certain data obtains and outputs the biopotential data, the acceleration data, and the angular rate data, or derivatives thereof, as discussed herein. The routine 900A may start at block 902, where the biopotential chip 250 may receive biopotential signals from a plurality of electrodes. At block 904, the biopotential chip 250 may convert the biopotential signals to biopotential data. At block 906, the biopotential chip 250 may receive, from an accelerometer disposed onboard the biopotential chip, acceleration data indicating an acceleration of the portion of the user's arm. At block 908, the biopotential chip 250 may receive, from a gyroscope disposed onboard the biopotential chip, angular rate data indicating an angular rate of the portion of the user's arm. At block 910, the biopotential chip 250 may output the biopotential data, the acceleration data, and the angular rate data, or derivatives thereof, to a machine learning classifier.

FIG. 9B depicts a flowchart of an exemplary routine 900B for switching connection states from a first connection state to a second connection state. In the routine 900B, the routine 900B may be performed by one or more systems, such as the biopotential chip 250 that performs the switch between different connection states, as discussed herein.

Figure 10:
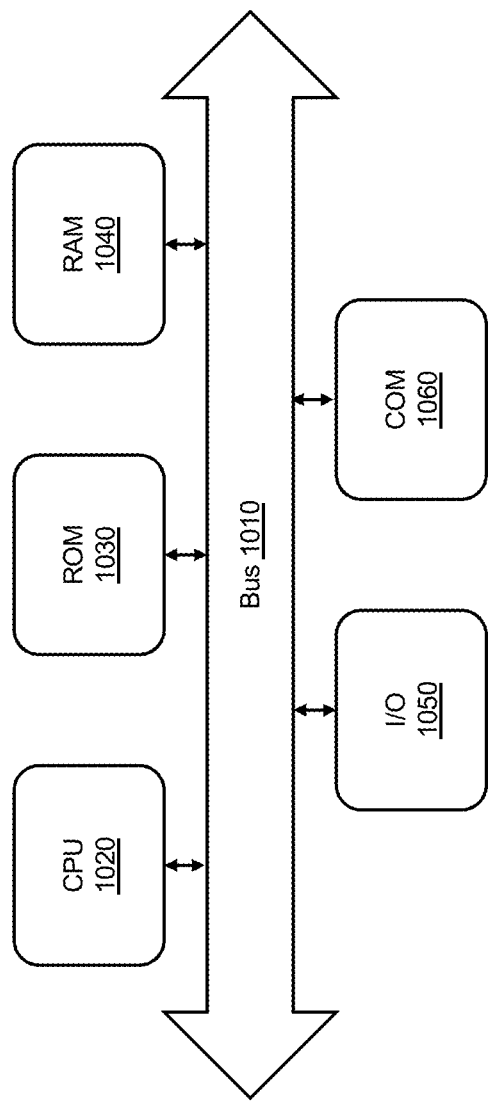
FIG. 10 depicts an example system that may execute techniques presented herein.

The routine 900B may start at block 912, where the biopotential chip 250 may apply, by a multiplexer, a first connection state, associated with a first mode, between a plurality of electrodes and a plurality of differential amplifiers. At block 914, the biopotential chip 250 may process biopotential signals in accordance with the first mode. For instance, the first mode may correspond to first one of obtain biopotential data, obtain training data, obtain ECG data, obtain impedance data, and the like, as discussed herein. At block 916, the biopotential chip 250 may determine to switch from the first connection state to a second connection state associated with a second mode. For instance, the biopotential chip 250 may receive an external command to switch modes. At block 918, the biopotential chip 250 may apply, by the multiplexer, the second connection state between the plurality of electrodes and the plurality of differential amplifiers. At block 920, the biopotential chip 250 may process biopotential signals in accordance with the second mode. For instance, the second mode may correspond to second one of obtain biopotential data, obtain training data, obtain ECG data, obtain impedance data, and the like, as discussed herein, Computer System FIG. 10 depicts an example system that may execute techniques presented herein. FIG. 10 is a simplified functional block diagram of a computer that may be configured to execute techniques described herein, according to exemplary cases of the present disclosure. Specifically, the computer (or "platform" as it may not be a single physical computer infrastructure) may include a data communication interface 1060 for packet data communication. The platform may also include a central processing unit 1020 ("CPU 1020"), in the form of one or more processors, for executing program instructions. The platform may include an internal communication bus 1010, and the platform may also include a program storage and/or a data storage for various data files to be processed and/or communicated by the platform such as ROM 1030 and RAM 1040, although the system 1000 may receive programming and data via network communications. The system 1000 also may include input and output ports 1050 to connect with input and output devices such as keyboards, mice, touchscreens, monitors, displays, etc. Of course, the various system functions may be implemented in a distributed fashion on a number of similar platforms, to distribute the processing load. Alternatively, the systems may be implemented by appropriate programming of one computer hardware platform.

The general discussion of this disclosure provides a brief, general description of a suitable computing environment in which the present disclosure may be implemented. In some cases, any of the disclosed systems, methods, and/or graphical user interfaces may be executed by or implemented by a computing system consistent with or similar to that depicted and/or explained in this disclosure. Although not required, aspects of the present disclosure are described in the context of computer-executable instructions, such as routines executed by a data processing device, e.g., a server computer, wireless device, and/or personal computer. Those skilled in the relevant art will appreciate that aspects of the present disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "server," and the like, are generally used interchangeably herein, and refer to any of the above devices and systems, as well as any data processor.

Aspects of the present disclosure may be embodied in a special purpose computer and/or data processor that is specifically programmed, configured, and/or constructed to perform one or more of the computer-executable instructions explained in detail herein. While aspects of the present disclosure, such as certain functions, are described as being performed exclusively on a single device, the present disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of the present disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the present disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Terminology

The terminology used above may be interpreted in its broadest reasonable manner, even though it is being used in conjunction with a detailed description of certain specific examples of the present disclosure. Indeed, certain terms may even be emphasized above; however, any terminology intended to be interpreted in any restricted manner will be overtly and specifically defined as such in this Detailed Description section. Both the foregoing general description and the detailed description are exemplary and explanatory only and are not restrictive of the features, as claimed.

As used herein, the terms "comprises," "comprising," "having," including," or other variations thereof, are intended to cover a non-exclusive inclusion such that a process, method, article, or apparatus that comprises a list of elements does not include only those elements, but may include other elements not expressly listed or inherent to such a process, method, article, or apparatus.

In this disclosure, relative terms, such as, for example, "about," "substantially," "generally," and "approximately" are used to indicate a possible variation of ±10% in a stated value.

The term "exemplary" is used in the sense of "example" rather than "ideal." As used herein, the singular forms "a," "an," and "the" include plural reference unless the context dictates otherwise.

Other aspects of the disclosure will be apparent to those skilled in the art from consideration of the specification and practice of the invention disclosed herein. It is intended that the specification and examples be considered as exemplary only, with a true scope and spirit of the invention being indicated by the following claims.

Examples

Clause 1. A system for gesture control, the system comprising: a wearable device configured to be worn on a portion of an arm of a user, the wearable device comprising: a plurality of electrodes disposed on an interior of the wearable device and configured to obtain biopotential signals from the user's arm; a biopotential microchip, the biopotential microchip comprising: a plurality of analog inputs configured to be coupled to and receive the biopotential signals from the plurality of electrodes, one or more of the plurality of analog inputs being coupled to respective differential amplifiers configured to amplify differences in signals between pairs of electrodes; a plurality of analog-to-digital converters (ADCs), the ADCs being configured to convert the biopotential signals to biopotential data; an accelerometer, the accelerometer being disposed onboard the biopotential microchip and configured to output acceleration data indicating an acceleration of the portion of the user's arm; a gyroscope, the gyroscope being disposed onboard the biopotential microchip and configured to output angular rate data indicating an angular rate of the portion of the user's arm; and a processor, the processor being configured to process the biopotential data outputted by the ADCs, the acceleration data outputted by the accelerometer, and the angular rate data outputted by the gyroscope; wherein the biopotential microchip is configured to output, directly or indirectly, the biopotential data outputted by the ADCs, the acceleration data outputted by the accelerometer, and the angular rate data outputted by the gyroscope, or derivatives thereof (collectively, the gesture data), to a machine learning classifier, the machine learning classifier being configured to generate, based on the gesture data, a gesture output indicating a gesture performed by the user.

Clause 2. The system of Clause 1, wherein the system further comprises a multiplexer, the multiplexer being configured to apply a plurality of connection states between the plurality of electrodes and the differential amplifiers, the system comprising: a first connection state in which a first pair of electrodes of the plurality of electrodes is connected to a first differential amplifier, the first differential amplifier being configured to amplify a difference in signals obtained by the first pair of electrodes in the first connection state; a second connection state in which a second pair of electrodes of the plurality of electrodes is connected to the first differential amplifier, the first differential amplifier being configured to amplify a difference in signals obtained by the second pair of electrodes in the second connection state; wherein at least one of the electrodes of the second pair of electrodes is not included in the first pair of electrodes.

Clause 3. The system of Clause 1, wherein the system further comprises: an electrocardiogram (ECG) microchip configured to analyze the biopotential signals obtained by one or more of the plurality of electrodes; and a multiplexer, the multiplexer being configured to apply a plurality of connection states; wherein the system comprises: a first connection state in which at a first electrode of the plurality of electrodes is electrically connected to the biopotential microchip; and a second connection state in which the first electrode is electrically connected to the ECG microchip.

Clause 4. The system of Clause 3, wherein the system is configured to: detect that the user has contacted an ECG electrode that is positioned on the wearable device such that the ECG electrode is not in contact with the user's arm when the wearable device is being worn on the arm; and in response to detecting that the user has contacted the ECG electrode, transition from the first connection state to the second connection state.

Clause 5. The system of any of Clauses 1-4, wherein the system is configured to enter an impedance measurement mode in which the system is configured to: apply a stimulus to a first electrode of the plurality of electrodes; analyze an impedance measurement signal using at least the first electrode and a second electrode of the plurality of electrodes, the impedance measurement signal comprising a response to the stimulus applied to the first electrode; and based on the impedance measurement signal, determine an impedance between the first electrode and the second electrode.

Clause 6. The system of Clause 5, wherein the system is further configured to: based on the determined impedance between the first electrode and the second electrode, present to the user an indication that signal quality is impaired.

Clause 7. The system of any of Clauses 1-6, wherein the biopotential microchip comprises: a low-power state in which the ADCs and the differential amplifiers are not enabled but the accelerometer and the gyroscope are enabled; and an active state in which each of the ADCs, the differential amplifiers, the accelerometer, and the gyroscope are enabled; wherein the biopotential microchip is configured to transition from the low-power state to the active state in response to an external command generated externally from the biopotential microchip and received by the biopotential microchip.

Clause 8. The system of any of Clauses 1-7, wherein the wearable device is a smartwatch and the plurality of electrodes are disposed in a circular arrangement on an inner surface of a hub of the smartwatch such that each of the plurality of electrodes is configured to contact a top of the user's arm when the smartwatch is worn.

Clause 9. The system of Clause 8, wherein the biopotential microchip is disposed in the hub of the smartwatch and at least one of the plurality of electrodes is a wristband electrode that is disposed on a wristband of the smartwatch, the wristband electrode being electrically coupled to the biopotential microchip disposed in the hub of the smartwatch.

Clause 10. The system of any of Clauses 1-9, wherein: the biopotential microchip is a first biopotential microchip and the wearable device comprises a second biopotential microchip; a first subset of the plurality of electrodes is coupled to the first biopotential microchip; a second subset of the plurality of electrodes is coupled to the second biopotential microchip; and the machine learning classifier is configured to generate the gesture output based on both the gesture data from the first biopotential microchip and data outputted by the second biopotential microchip.

Clause 11. The system of Clause 10, wherein the biopotential microchip has a low-power state in which the accelerometer and the gyroscope are powered down but at least the ADCs are active.

Clause 12. The system of any of Clauses 1-9, wherein the processor is configured to encrypt and/or normalize the gesture data.

Clause 13. Clause 1. A system for gesture control, the system comprising: a wearable device configured to be worn on a wrist of a user, the wearable device comprising: a hub, the hub comprising: a sealed housing; a plurality of hub electrodes; and a biopotential microchip, the biopotential microchip comprising a plurality of analog inputs, a plurality of analog-to-digital converters (ADCs) configured to receive signals from the plurality of analog inputs, an accelerometer, and a gyroscope; a wristband, the wristband and the hub together being configured to encircle the wrist of the user, the wristband comprising one or more wristband electrodes; wherein: the sealed housing of the hub comprises an electrical port, the electrical port being electrically connected to at least a first analog input of the plurality of analog inputs of the biopotential microchip; the wristband comprises one or more wristband conductors, the one or more wristband conductors electrically connecting the one or more wristband electrodes to the electrical port of sealed housing of the hub; the plurality of hub electrodes are electrically connected via conductors disposed within the hub to one or more additional analog inputs of the plurality of analog inputs of the biopotential microchip, and the one or more wristband electrodes are electrically connected to at least the first analog input of the plurality of analog inputs of the biopotential microchip via the wristband conductor and the electrical port of the sealed housing of the hub; the system is configured to obtain biopotential data based on signals received by both the plurality of hub electrodes and the one or more wristband electrodes and processed by the ADCs of the biopotential microchip; the system is configured to obtain wrist location data based on outputs from the accelerometer and the gyroscope; and the system is configured to transmit the biopotential data and the wrist location data to a machine learning classifier, the machine learning classifier being configured to analyze the biopotential data and the wrist location data to generate a gesture output indicating a gesture performed by the user.

Clause 14. The system of Clause 13, wherein the hub electrodes are disposed in a curved arrangement, the curved arrangement having a curvature in a plane that extends perpendicular to a length of the forearm when the wearable device is worn on the wrist.

Clause 15. The system of any of Clauses 13-14, wherein the one or more wristband electrodes are coupled to one or more wristband amplifiers, the one or more wristband amplifiers being disposed between the one or more wristband electrodes and the one or more wristband conductors, the one or more wristband amplifiers being configured to amplify signals received by the one or more wristband electrodes to buffer the signals from noise and/or interference as the signals travel through the one or more wristband conductors.

Clause 16. The system of any of Clause 13-15, wherein the wristband is adjustable to a plurality of length states, each of the plurality of length states having a respective circumference when the wristband is worn.

Clause 17. The system of Clause 16, wherein the one or more wristband electrodes is configured to be situated at a constant position relative to the hub in each of the plurality of length states, such that the one or more wristband electrodes are disposed at a predetermined position on the user's wrist across a range of wrist sizes.

Clause 18. The system of Clause 17, wherein the wristband connects to the hub on two sides of the hub, the wristband being adjustable relative to the hub on both of the two connections between the wristband and the hub.

Clause 19. The system of any of Clauses 13-18, wherein the one or more wristband conductors comprise a conductive fabric.

Clause 20. The system of any of Clauses 13, 13-19, wherein the system further comprises: an electrocardiogram (ECG) microchip configured to analyze biopotential signals obtained by one or more of the plurality of hub electrodes and/or the one or more wristband electrodes; and a multiplexer, the multiplexer being configured to apply a plurality of connection states; wherein the system comprises: a first connection state in which at a first electrode of the plurality of hub electrodes and/or the one or more wristband electrodes is electrically connected to the biopotential microchip; and a second connection state in which the first electrode is electrically connected to the ECG microchip.

The invention claimed is:

1. A system, the system comprising:
  a wearable device configured to be worn on a portion of an arm of a user, the wearable device comprising:
    a plurality of electrodes disposed on an interior of the wearable device and configured to obtain biopotential signals from the user's arm;
    a biopotential microchip, the biopotential microchip comprising:
      one or more analog inputs configured to be coupled to and receive the biopotential signals from the plurality of electrodes, at least one of the one or more analog inputs being coupled to a respective differential amplifier configured to amplify differences in signals between pairs of electrodes;
      one or more analog-to-digital converters (ADCs), the one or more ADCs being configured to convert the biopotential signals to biopotential data;
      an accelerometer, the accelerometer being disposed onboard the biopotential microchip and configured to output acceleration data indicating an acceleration of the portion of the user's arm;
      a gyroscope, the gyroscope being disposed onboard the biopotential microchip and configured to output angular rate data indicating an angular rate of the portion of the user's arm; and
      a processor, the processor being configured to process the biopotential data outputted by the one or more ADCs, the acceleration data outputted by the accelerometer, and the angular rate data outputted by the gyroscope;
    wherein the biopotential microchip is an integral unit and has all of the processor, the gyroscope, the accelerometer, the one or more analog inputs, the ADCs, located on a common unitary substrate,
    wherein the biopotential microchip is configured to output, directly or indirectly, the biopotential data outputted by the one or more ADCs, the acceleration data outputted by the accelerometer, and the angular rate data outputted by the gyroscope, or derivatives thereof (collectively, data), to a machine learning classifier, the machine learning classifier being configured to generate, based on the data, an output indicating a parameter of the user,
    wherein the biopotential microchip comprises either:
      (a) a first low-power state in which the one or more ADCs and the differential amplifiers are not enabled but the accelerometer and the gyroscope are enabled; and an active state in which each of the one or more ADCs, the differential amplifiers, the accelerometer, and the gyroscope are enabled, or
      (b) a second low-power state in which the accelerometer and the gyroscope are powered down but at least the one or more ADCs are active.

2. The system of claim 1, wherein the system further comprises a multiplexer, the multiplexer being configured to apply a plurality of connection states between the plurality of electrodes and the differential amplifiers, the system comprising:
  a first connection state in which a first pair of electrodes of the plurality of electrodes is connected to a first differential amplifier, the first differential amplifier being configured to amplify a difference in signals obtained by the first pair of electrodes in the first connection state;
  a second connection state in which a second pair of electrodes of the plurality of electrodes is connected to the first differential amplifier, the first differential amplifier being configured to amplify a difference in signals obtained by the second pair of electrodes in the second connection state;
  wherein at least one of the electrodes of the second pair of electrodes is not included in the first pair of electrodes.

3. The system of claim 1, wherein the system further comprises:
  an electrocardiogram (ECG) microchip configured to analyze the biopotential signals obtained by one or more of the plurality of electrodes; and
  a multiplexer, the multiplexer being configured to apply a plurality of connection states;
  wherein the system comprises:
  a first connection state in which at a first electrode of the plurality of electrodes is electrically connected to the biopotential microchip; and
  a second connection state in which the first electrode is electrically connected to the ECG microchip.

4. The system of claim 3, wherein the system is configured to:
  detect that the user has contacted an ECG electrode that is positioned on the wearable device such that the ECG electrode is not in contact with the user's arm when the wearable device is being worn on the arm; and in response to detecting that the user has contacted the ECG electrode, transition from the first connection state to the second connection state.

5. The system of claim 1, wherein the system is configured to enter an impedance measurement mode in which the system is configured to:
apply a stimulus to a first electrode of the plurality of electrodes;
analyze an impedance measurement signal using at least the first electrode and a second electrode of the plurality of electrodes, the impedance measurement signal comprising a response to the stimulus applied to the first electrode; and
based on the impedance measurement signal, determine an impedance between the first electrode and the second electrode.

6. The system of claim 5, wherein the system is further configured to:
based on the determined impedance between the first electrode and the second electrode, present to the user an indication that signal quality is impaired.

7. The system of claim 1, wherein
the first low-power state has the one or more ADCs and the differential amplifiers not enabled and the accelerometer and the gyroscope enabled; and
wherein the biopotential microchip is configured to transition from the first low-power state to the active state in response to an external command generated externally from the biopotential microchip and received by the biopotential microchip.

8. The system of claim 1, wherein the wearable device is a smartwatch, the plurality of electrodes are disposed in a circular arrangement on an inner surface of a hub of the smartwatch such that each of the plurality of electrodes is configured to contact a top of the user's arm when the smartwatch is worn, the hub is a case of the smartwatch.

9. The system of claim 8, wherein the biopotential microchip is disposed in the hub of the smartwatch, a first set of the plurality of electrodes are hub electrodes are disposed in the circular arrangement on the inner surface of the hub, a second set of the plurality of electrodes are wristband electrodes are disposed on a wristband of the smartwatch, the wristband electrodes are electrically coupled to the biopotential microchip disposed in the hub of the smartwatch, and the hub electrodes are spaced apart from the wristband electrodes, so that hub electrodes and the wristband electrodes contact different portions of the user's arm.

10. The system of claim 1, wherein:
the biopotential microchip is a first biopotential microchip and the wearable device comprises a second biopotential microchip;
a first subset of the plurality of electrodes is coupled to the first biopotential microchip;
a second subset of the plurality of electrodes is coupled to the second biopotential microchip; and
the machine learning classifier is configured to generate the output based on both the data from the first biopotential microchip and data outputted by the second biopotential microchip.

11. The system of claim 10, wherein the second low-power state has the accelerometer and the gyroscope powered down but at least the one or more ADCs are active.

12. The system of claim 1, wherein the processor is configured to encrypt and/or normalize the data before the data is transmitted off the biopotential microchip.

13. A method, the method comprising:
receiving, by one or more analog inputs of a biopotential microchip, biopotential signals from a plurality of electrodes, at least one of the one or more analog inputs being coupled to a respective differential amplifier of the biopotential microchip, the differential amplifier being configured to amplify differences in signals between pairs of electrodes;
converting, by one or more analog-to-digital converters (ADCs) of the biopotential microchip, the biopotential signals to biopotential data;
obtaining and outputting, by an accelerometer disposed onboard the biopotential microchip, acceleration data indicating an acceleration of a portion of an arm of a user;
obtaining and outputting, by a gyroscope disposed onboard the biopotential microchip, angular rate data indicating an angular rate of the portion of the aim of the user; and
processing, by a processor of the biopotential microchip, the biopotential data outputted by the one or more ADCs, the acceleration data outputted by the accelerometer, and the angular rate data outputted by the gyroscope;
wherein the biopotential microchip is an integral unit and has all of the processor, the gyroscope, the accelerometer, the one or more analog inputs, the ADCs, located on a common unitary substrate,
wherein the biopotential microchip is configured to output, directly or indirectly, the biopotential data outputted by the one or more ADCs, the acceleration data outputted by the accelerometer, and the angular rate data outputted by the gyroscope, or derivatives thereof (collectively, data), to a classifier, the classifier being configured to generate, based on the data, an output indicating a parameter of the user,
wherein the biopotential microchip comprises either:
(a) a first low-power state in which the one or more ADCs and the differential amplifiers are not enabled but the accelerometer and the gyroscope are enabled; and an active state in which each of the one or more ADCs, the differential amplifiers, the accelerometer, and the gyroscope are enabled, or
(b) a second low-power state in which the accelerometer and the gyroscope are powered down but at least the one or more ADCs are active.

14. The method of claim 13, further comprising:
applying, by a multiplexer of the biopotential microchip, a plurality of connection states between the plurality of electrodes and the differential amplifiers, the plurality of connection states comprising:
a first connection state in which a first pair of electrodes of the plurality of electrodes is connected to a first differential amplifier, the first differential amplifier being configured to amplify a difference in signals obtained by the first pair of electrodes in the first connection state;
a second connection state in which a second pair of electrodes of the plurality of electrodes is connected to the first differential amplifier, the first differential amplifier being configured to amplify a difference in signals obtained by the second pair of electrodes in the second connection state;
wherein at least one of the electrodes of the second pair of electrodes is not included in the first pair of electrodes.

15. The method of claim 13, further comprising:
analyzing, by an electrocardiogram (ECG) microchip, the biopotential signals obtained by one or more of the plurality of electrodes; and
applying, by a multiplexer of the biopotential microchip, a plurality of connection states between the plurality of electrodes and the differential amplifiers, the plurality of connection states comprising:
a first connection state in which at a first electrode of the plurality of electrodes is electrically connected to the biopotential microchip; and
a second connection state in which the first electrode is electrically connected to the ECG microchip.

16. The method of claim 15, further comprising:
detecting an ECG trigger; and
in response to detecting the ECG trigger, transitioning from the first connection state to the second connection state.

17. The method of claim 13, further comprising, when the biopotential microchip is in an impedance measurement mode:
applying a stimulus to a first electrode of the plurality of electrodes;
analyzing an impedance measurement signal using at least the first electrode and a second electrode of the plurality of electrodes, the impedance measurement signal comprising a response to the stimulus applied to the first electrode; and
based on the impedance measurement signal, determining an impedance between the first electrode and the second electrode.

18. The method of claim 17, further comprising:
based on the determined impedance between the first electrode and the second electrode, presenting to the user an indication that signal quality is impaired.

19. The method of claim 13, further comprising:
transitioning from the first low-power state to the active state in response to an external command generated externally from the biopotential microchip and received by the biopotential microchip,
wherein the first low-power state has the one or more ADCs and the differential amplifiers not enabled and the accelerometer and the gyroscope enabled.

20. A biopotential microchip comprising:
one or more analog inputs configured to be coupled to and receive biopotential signals from a plurality of electrodes, at least one of the one or more analog inputs being coupled to a respective differential amplifier configured to amplify differences in signals between pairs of electrodes;
one or more analog-to-digital converters (ADCs), the one or more ADCs being configured to convert the biopotential signals to biopotential data;
an accelerometer, the accelerometer being disposed onboard the biopotential microchip and configured to output acceleration data indicating an acceleration of a portion of a user's arm;
a gyroscope, the gyroscope being disposed onboard the biopotential microchip and configured to output angular rate data indicating an angular rate of the portion of the user's arm; and
a processor, the processor being configured to process the biopotential data outputted by the one or more ADCs, the acceleration data outputted by the accelerometer, and the angular rate data outputted by the gyroscope;
wherein the biopotential microchip is an integral unit and has all of the processor, the gyroscope, the accelerometer, the one or more analog inputs, the ADCs, located on a common unitary substrate,
wherein the biopotential microchip is configured to output, directly or indirectly, the biopotential data outputted by the one or more ADCs, the acceleration data outputted by the accelerometer, and the angular rate data outputted by the gyroscope, or derivatives thereof (collectively, data), to a classifier, the classifier being configured to generate, based on the data, an output indicating a parameter of the user,
wherein the biopotential microchip comprises either:
(a) a first low-power state in which the one or more ADCs and the differential amplifiers are not enabled but the accelerometer and the gyroscope are enabled; and an active state in which each of the one or more ADCs, the differential amplifiers, the accelerometer, and the gyroscope are enabled, or
(b) a second low-power state in which the accelerometer and the gyroscope are powered down but at least the one or more ADCs are active.

* * * * *